United States Patent
Levinsohn et al.

(10) Patent No.: US 10,363,026 B2
(45) Date of Patent: Jul. 30, 2019

(54) ROTATING SUTURE ANCHOR

(71) Applicant: Fusion Orthopedics, LLC, Mesa, AZ (US)

(72) Inventors: David Gordon Levinsohn, San Diego, CA (US); Hugh Sharkey, San Francisco, CA (US)

(73) Assignee: Fusion Orthopedics, LLC, Mesa, AZ (US)

( * ) Notice: Subject to any disclaimer, the term of this patent is extended or adjusted under 35 U.S.C. 154(b) by 243 days.

(21) Appl. No.: 15/330,580

(22) Filed: Oct. 14, 2016

(65) Prior Publication Data
US 2017/0231617 A1    Aug. 17, 2017

(51) Int. Cl.
*A61B 17/04*    (2006.01)

(52) U.S. Cl.
CPC ...... *A61B 17/0401* (2013.01); *A61B 17/0483* (2013.01); *A61B 2017/0403* (2013.01); *A61B 2017/045* (2013.01); *A61B 2017/0409* (2013.01); *A61B 2017/0412* (2013.01); *A61B 2017/0414* (2013.01)

(58) Field of Classification Search
CPC .................................................. A61B 17/0401
See application file for complete search history.

(56) References Cited

U.S. PATENT DOCUMENTS

| | | | |
|---|---|---|---|
| 5,601,557 A | 2/1997 | Hayhurst | |
| 8,414,613 B2 | 4/2013 | Huxel | |
| 9,345,467 B2 | 5/2016 | Lunn | |
| 2006/0282081 A1 | 12/2006 | Fanton et al. | |
| 2008/0125815 A1* | 5/2008 | Heaven | A61B 17/0401 606/308 |
| 2009/0312793 A1* | 12/2009 | Huxel | A61B 17/0401 606/232 |
| 2010/0305610 A1 | 12/2010 | Kim et al. | |
| 2011/0009884 A1 | 1/2011 | Kaplan | |
| 2012/0071877 A1 | 3/2012 | Frigg | |
| 2013/0296937 A1 | 11/2013 | Dreyfuss et al. | |

OTHER PUBLICATIONS

Copenheaver, Blaine R.; PCT App. No. PCT/US20171050623; International Search Report and Written Opinion; dated Nov. 7, 2017; 9 pages.

* cited by examiner

*Primary Examiner* — Tuan V Nguyen

(57) ABSTRACT

A top locking rotatable suture anchor device secures one or more sutures with the suture anchor device, installed within a bone at a surgical treatment site, providing rotation of the suture while secured within the suture anchor device and providing adjustment to the tension of the suture during the surgical procedure, the suture anchor device including a delivery tool cooperating with the suture device to conduct the installation of the suture anchor device and tensioning of the suture within suture anchor device.

23 Claims, 21 Drawing Sheets

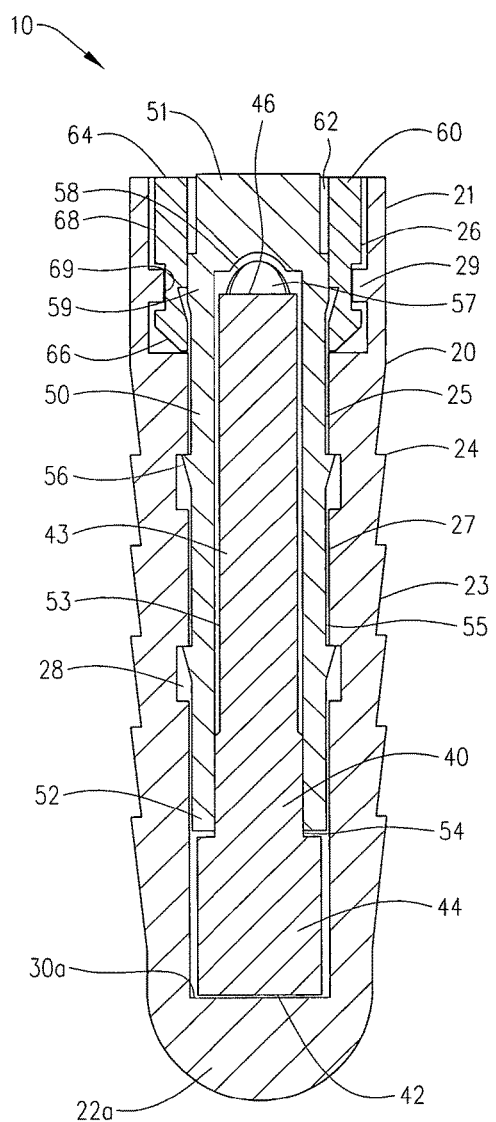
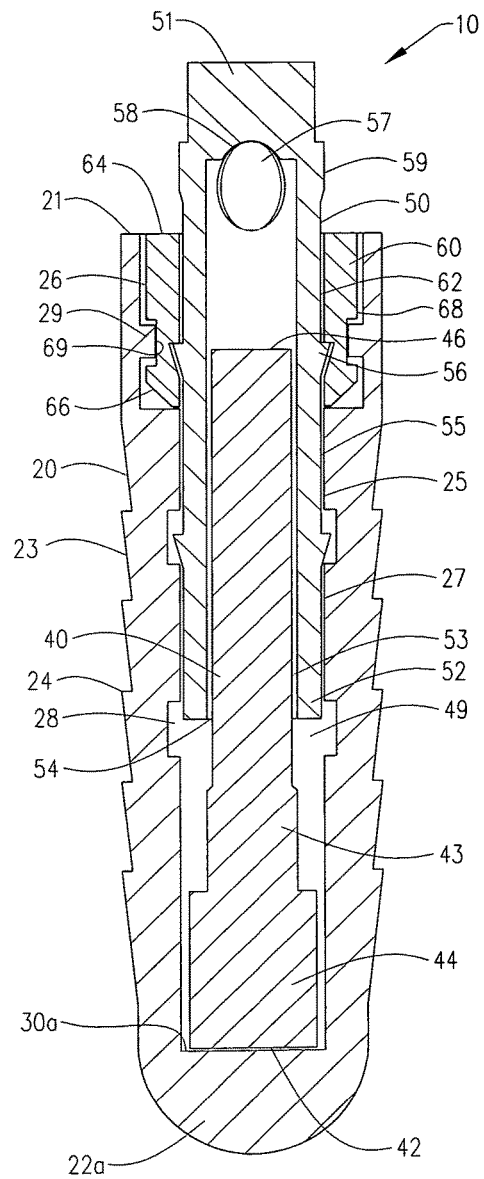

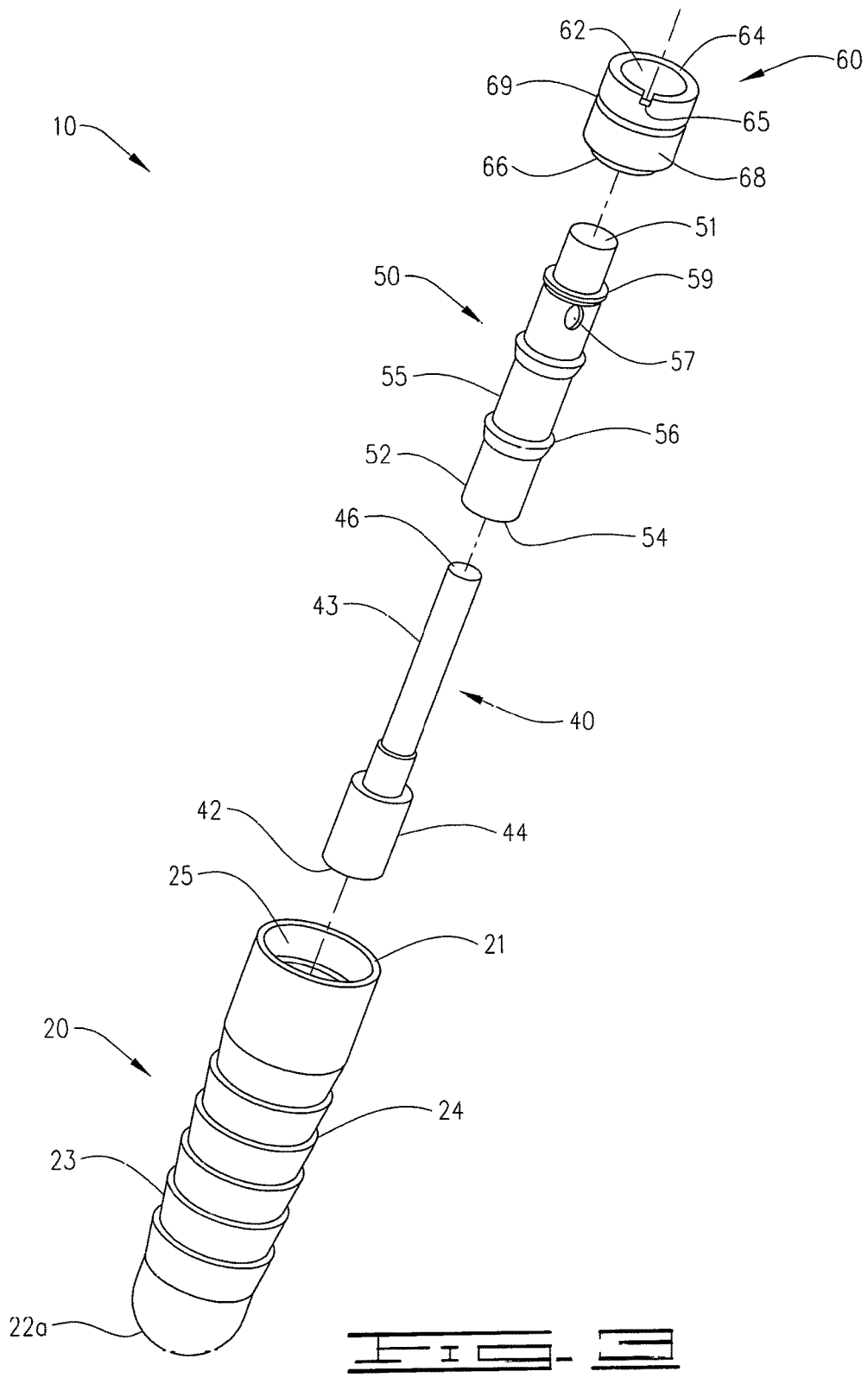

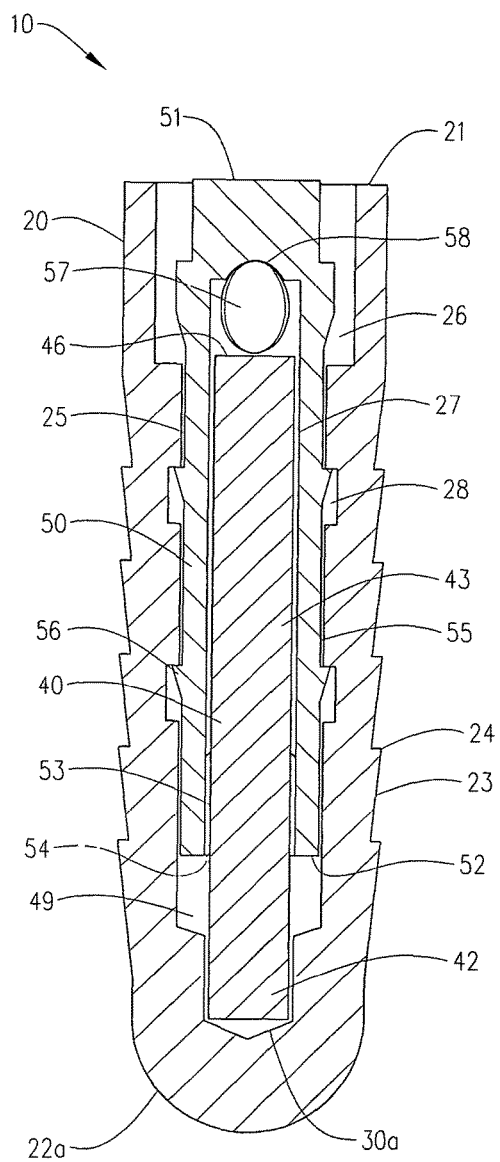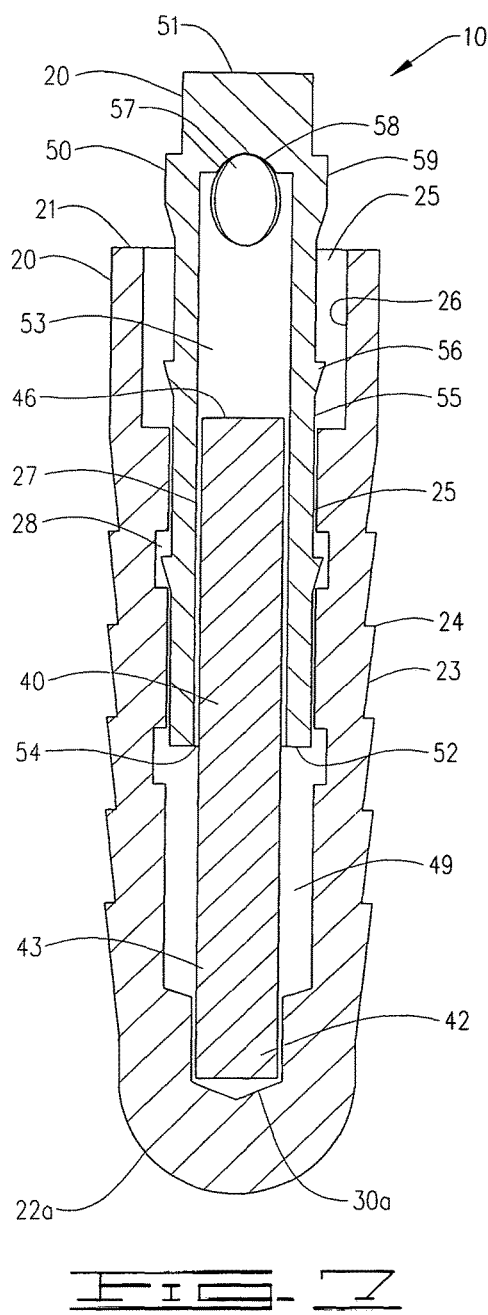

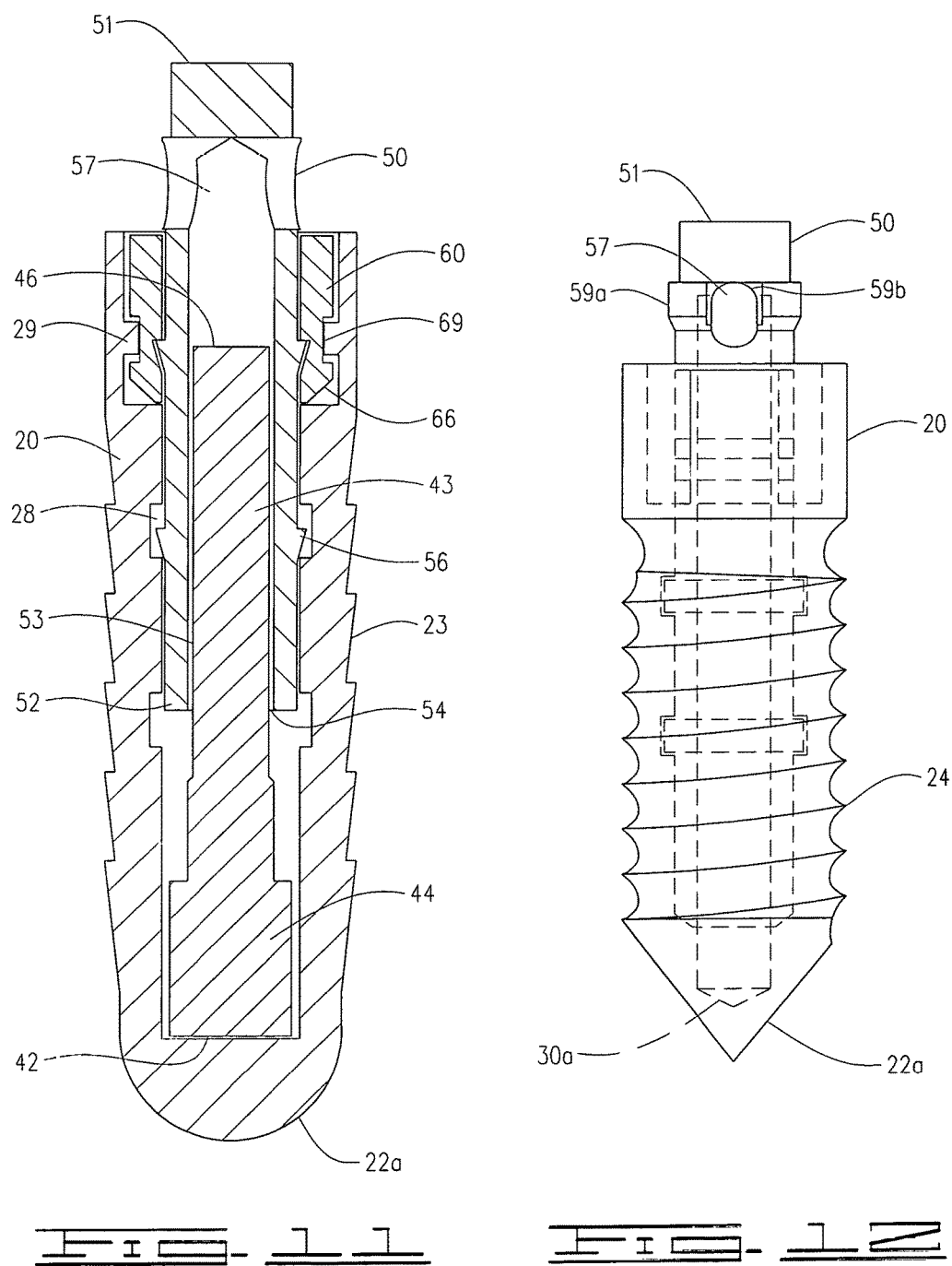

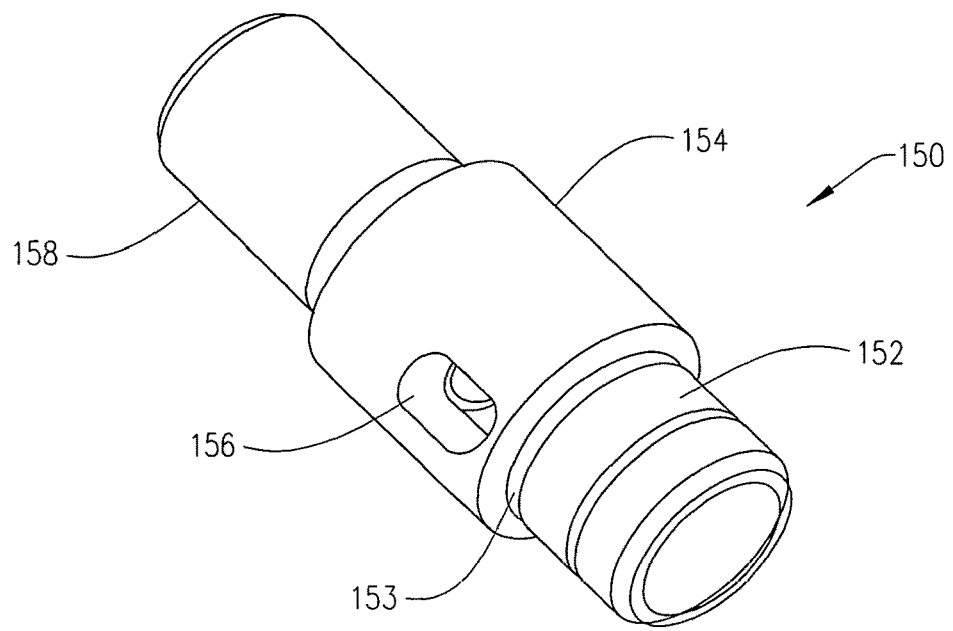
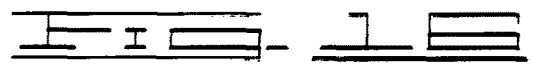
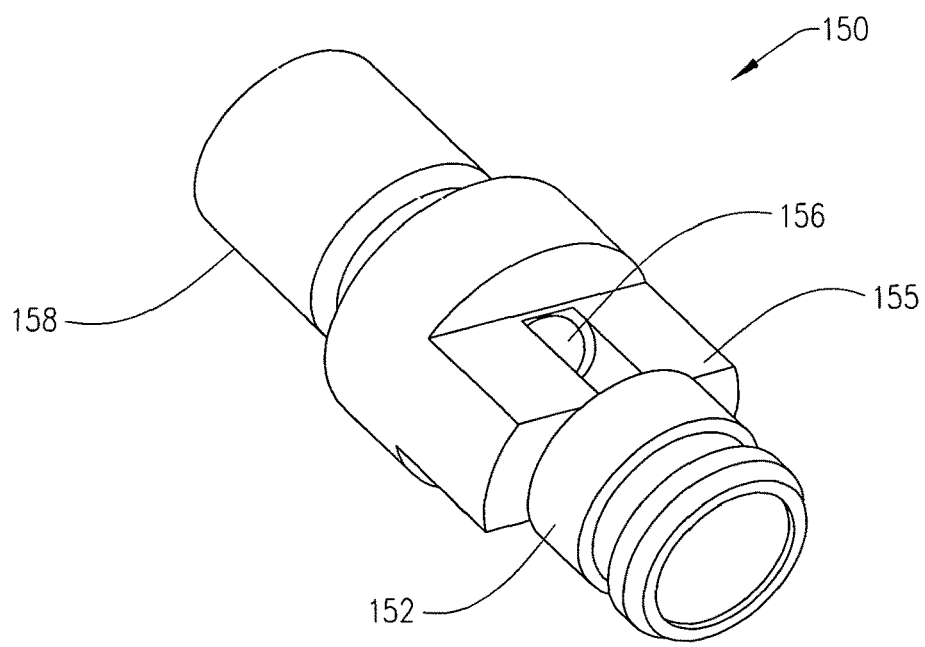
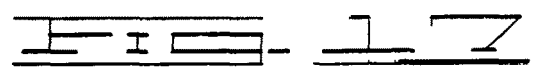

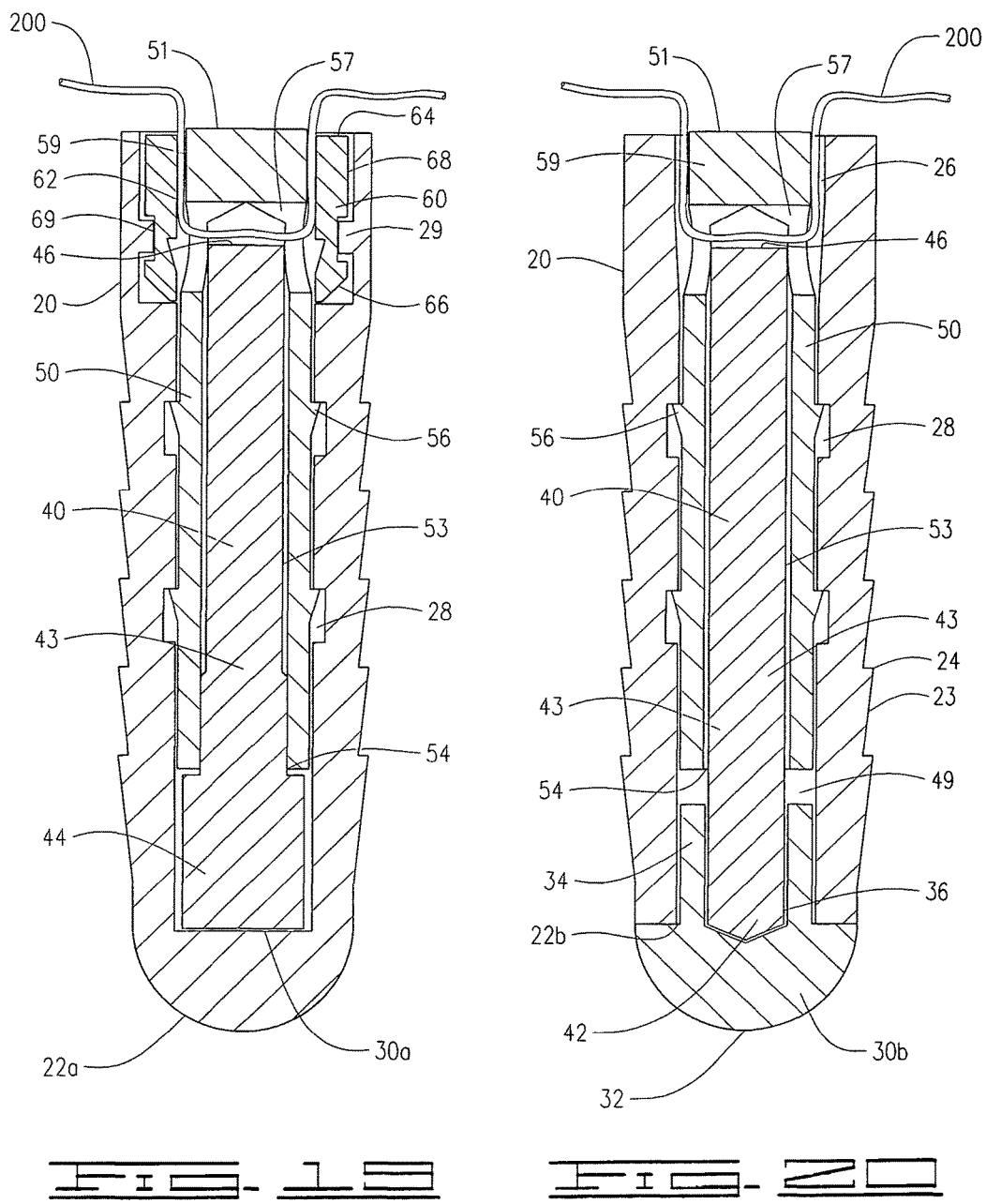

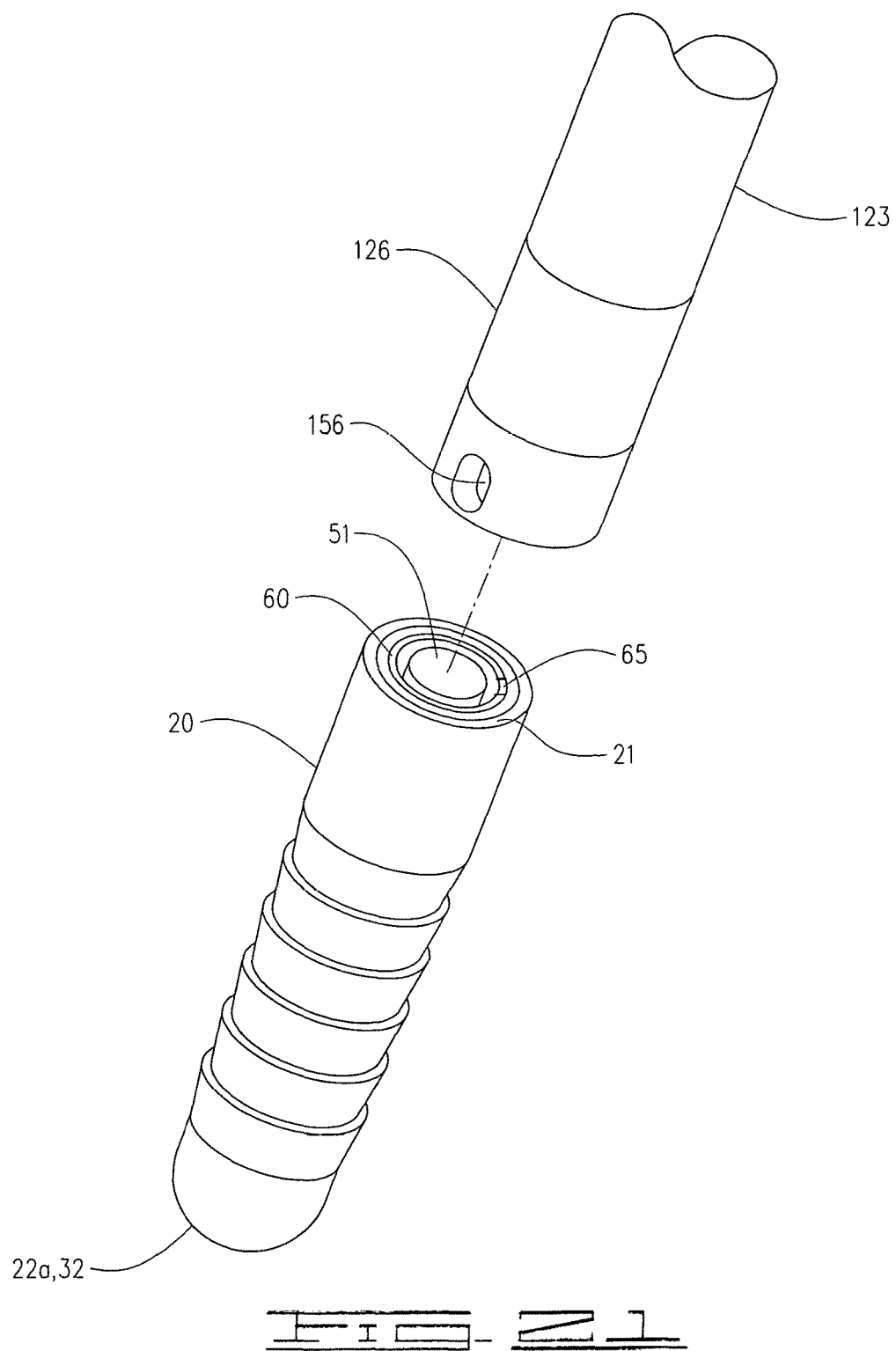

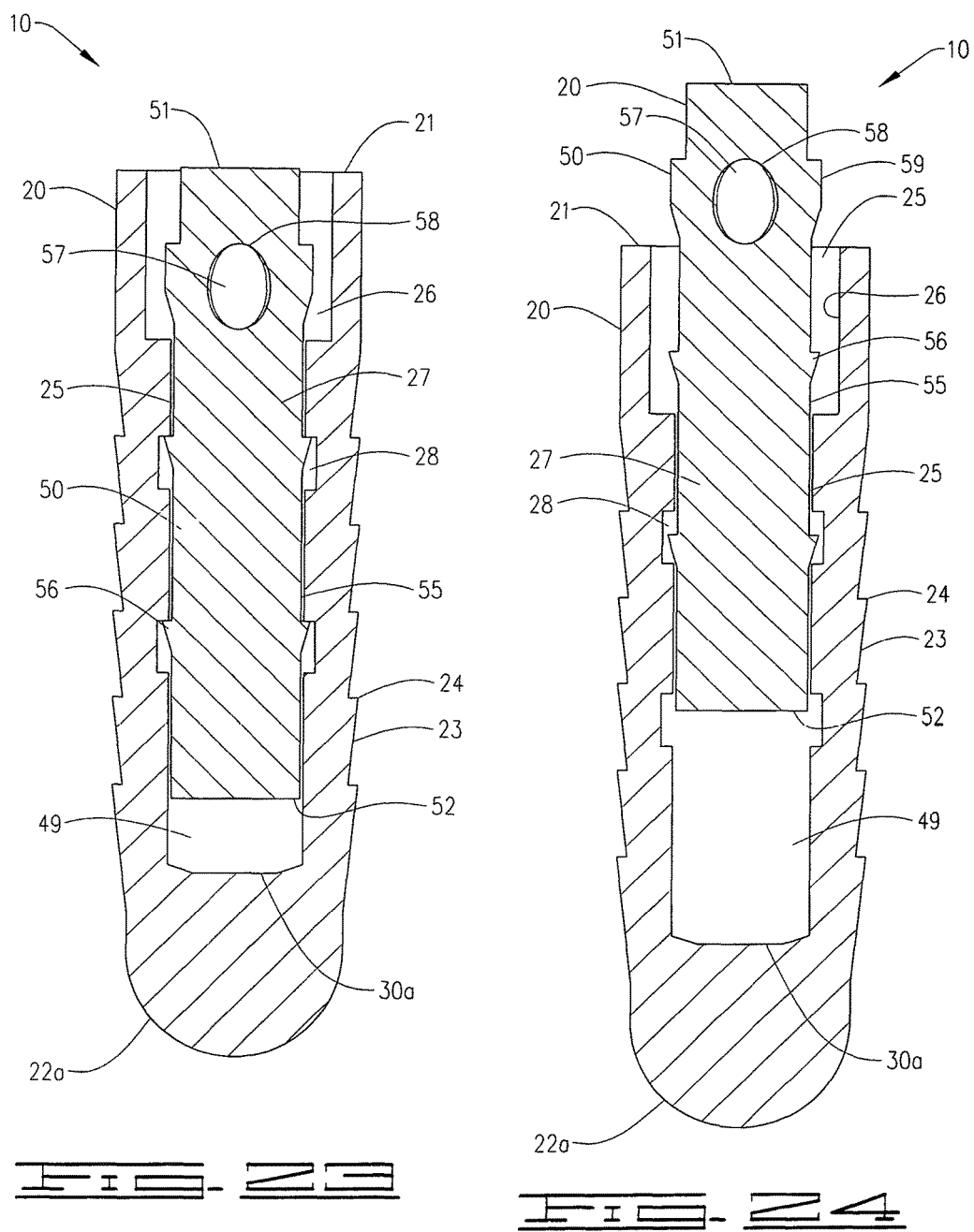

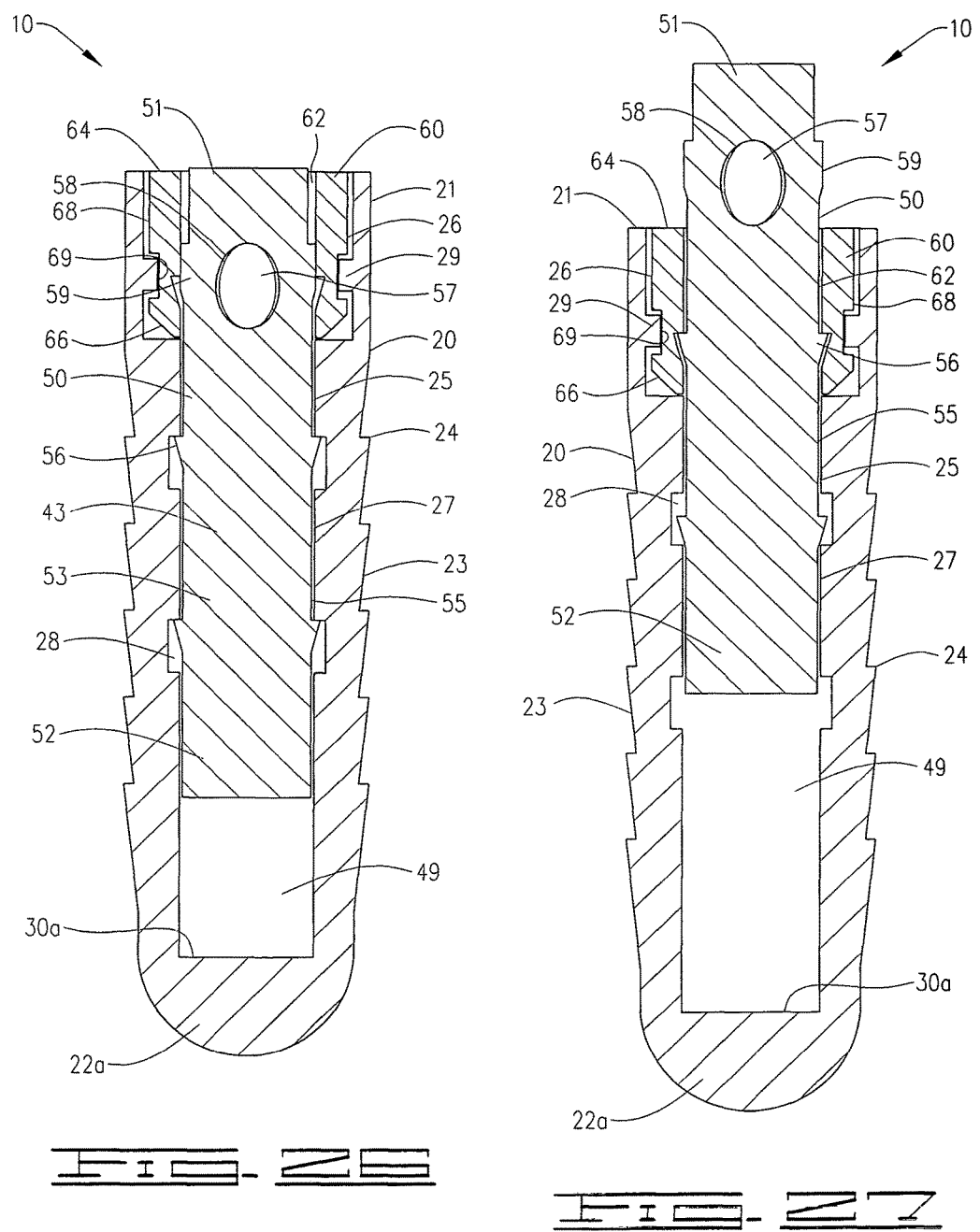

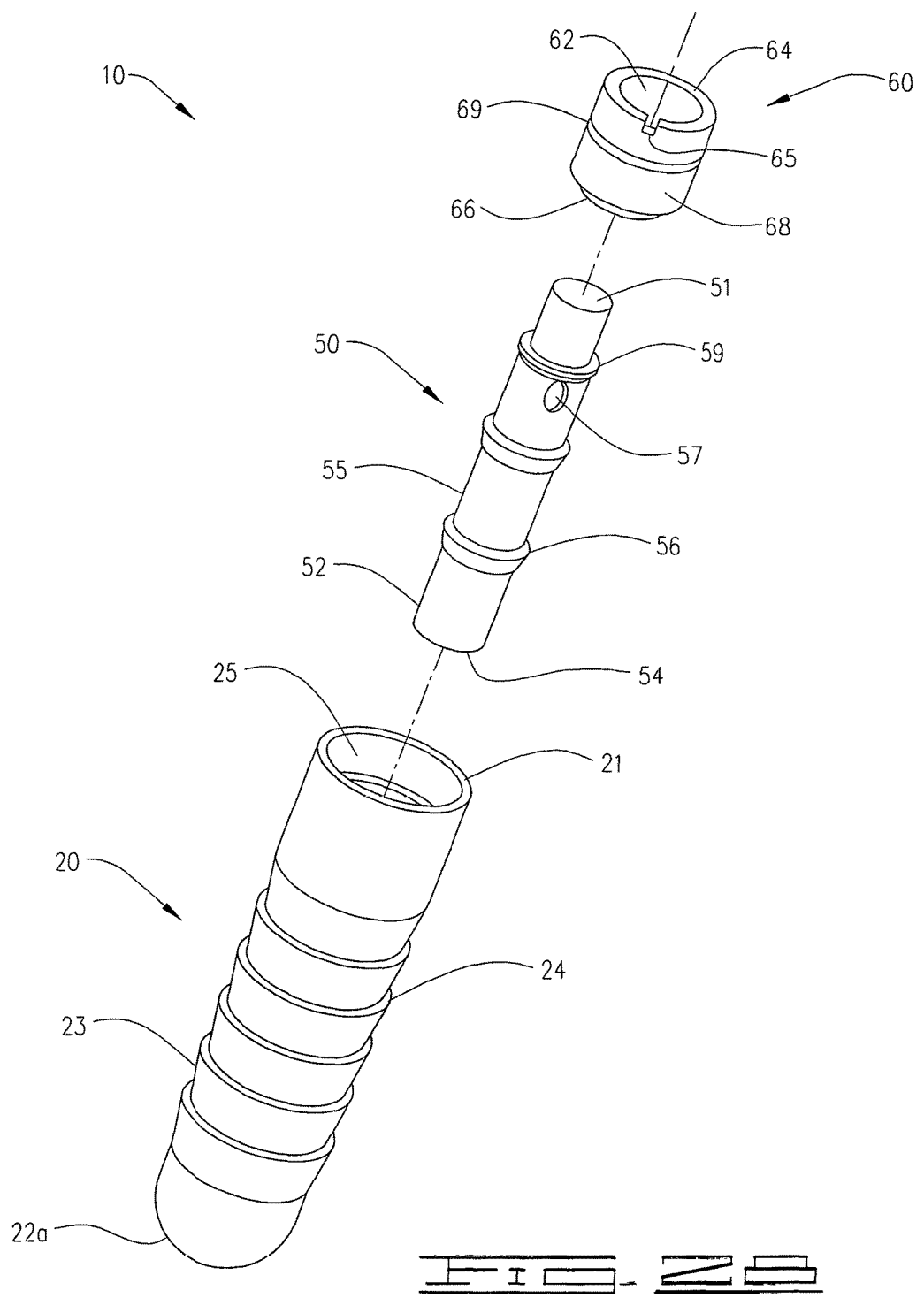

ROTATING SUTURE ANCHOR

CROSS REFERENCE TO RELATED APPLICATIONS

Applicant claims the benefit of the previously filed provisional patent application, U.S. Patent Ser. No. 62/294,662, filed on Feb. 12, 2016, by the same inventor.

I. BACKGROUND OF THE INVENTION

1. Field of Invention

A top locking suture anchor and installation tool for use during several types of orthopedic surgical procedures provides the suture anchor to attach soft tissue to bone, the present suture anchor providing for rotation of an attached suture to properly align the suture with the soft tissue in the installed suture anchor, adjusting the tension of the suture, and securing the suture, with or without tying or knotting of the suture, with the secured or unsecured suture being free to rotate radially, reducing the stress on the suture and soft tissue being repaired.

2. Description of Prior Art

A preliminary review of prior art patents was conducted by the applicant which reveal prior art patents in a similar field or having similar use. However, the prior art inventions do not disclose the same or similar elements as the present rotatable suture anchor, nor do they present the material components in a manner contemplated or anticipated in the prior art.

In U.S. Pat. No. 5,601,557 to Hayhurst, a method patent discloses a suture anchor uses a deformable plug inserted within an anchor (FIGS. 15-21) to capture an end of a suture. There appears to be no threading through the eyelet pin, transverse passage or roof, nor a capture at multiple points along the threaded suture, including a location between the enlarged portion of the eyelet pin and a rotating or rotatable ring or any tapered leading end of the rotatable ring.

The suture anchor of U.S. Patent Publication No. 2011/0009884 to Kaplan discloses an anchor having an inner surface and an outer surface that may or may not have threads to secure a plug with a friction fit between the plug and the inner surface. The plug has an outer wall having threads such that when a suture is draped into the anchor, the plug secures the sutures via a friction fit between the plug and the inner surface of the wall. Once again, the Kaplan patent, like the Hayhurst patent is a utility patent presented as a method patent In U.S. Pat. No. 8,414,613 to Huxel and the present inventor, David Levinsohn, a suture anchor defines a main anchor body defining a longitudinal axis and having a external formation for securing the anchor to a bone and a receiving formation, an eyelet pin defining a longitudinal axis with a transverse passage through which a suture can be threaded with the pin having an open and closed position with the eyelet pin having a lower bore, and a central pin disposed in the receiving formation upon which the lower bore of the eyelet pin slides, with some interference fit between the lower bore of the eyelet pin and the central pin. It also provides the central pin and the eyelet pin as freely rotatable about their longitudinal axis relative to the main anchor body. Huxel also claimed a suture anchor presented to the surgeon with one or more sutures locked in the eyelet pin in the closed position with the sutures not free to slide, compared to the present device where the sutures are presented to the surgeon with the sutures free to slide within the suture anchor device.

Huxel does not present a rotating ring, a frangible connector including a rotating ring, a similar delivery tool allowing for the adjustment of a connected suture, and Huxel does not contain an embodiment void of a central pin. Huxel presented a no rotating locking C-ring disposed in the upper part of the inner wall of the anchor body that allowed ramp formations in the far end of the eyelet pin to pass through the C-ring and thus secure the eyelet pin from migrating out the inner body of the anchor. Rotation of the suture about the longitudinal axis was dependent on the lack of compression of the suture on the inner wall of the non rotating C-ring as the suture exited from the eyelet. The eyelet pin of Huxel did not have a pin lock extension formation that articulated with the inner locking grooves of the anchor body, nor did the eyelet pin include formations to capture the exiting suture from the eyelet.

U.S. Pat. No. 9,345,467 to Lunn provides a bone anchor assembly for orthopedic installation defining, " . . . an anchor defining a cavity with a proximal portion and a distal portion, the proximal portion having a larger diameter than the distal portion and an opening to the cavity, a transverse through hole extending through the anchor, the through hole having openings at each end of the through hole that open to an outer surface of the anchor, the cavity extending into the through hole, and an insertion member configured for arrangement within the anchor cavity, the insertion member including a body having a proximal end portion and a flat distal end portion and a head coupled to the proximal end portion of the body, wherein the anchor includes protrusions located on an outer surface of the anchor and below the through hole openings, the protrusions tapered along their lengths and extending away from the outer surface of the anchor, the protrusions arranged on the outer surface such that the non tapered areas are located between the protrusions, the protrusions configured to facilitate loading of a flexible member (suture) into the anchor, wherein the non-tapered areas are rounded." (Claim 1) Basically, the anchor goes into the bored hole in the bone, with the suture through the transverse through hole with the suture extending back to the proximal ends. The suture attaches to the soft tissue and is drawn towards the imbedded anchor. When the suture is at the desired length and the soft tissue tension is appropriate, the surgeon, using a tool, inserts the insertion member into the cavity until the suture is captured. The additional features include side slots in the anchor, barbs on the outer surface of the anchor, one suture through the through hole, a threaded cavity, head of the insertion member configured for a tool, insertion member secures the suture within the through hole, more than one suture in the through hole the flexible member is a suture, slots extend from the transverse through hole to the proximal portion of the anchor, barbs intersect slots, and the through hole openings being aligned. None of the prior art discloses a knotless rotating suture anchor having an anchor body with inner locking grooves that articulate with pin lock extensions on the eyelet pin, a rotatable ring secured within the anchor body and the various locking means as disclosed on the eyelet pin of the present suture anchor device.

None of the prior art discloses a four component suture anchor comprising an anchor body, a central pin, an eyelet pin and a rotating ring. None of the prior art discloses a rotatable suture anchor comprising an anchor body, eyelet pin and rotating ring. None of the prior art comprises a rotatable suture anchor defining a simple two component product defining an anchor body and an eyelet pin while still providing rotation and sliding of a suture in a closed position.

The two piece device, as well as the three and four component devices further improve the prior art and provide significant clinical benefit that includes the ability of the surgeon to tie one of many sliding slip knot variations versus Huxel's surgeon's knot due to the Huxel non sliding suture requirements. The knotless rotatable capacity of the present suture anchor devices provide enhanced suture retention due to increased surface area for suture capture versus the interaction of the central pin with the eyelet pin of Huxel, providing the advantages of the ability to capture more than one suture, multiple suture ends per implant resulting in greater usefulness to a surgeon, and a more simple design with less components per suture resulting in more economically feasible cost of goods. The presence or absence of the central pin may be determined under certain conditions chosen by the surgeon for enhanced capture of the suture. The rotatable ring, likewise, may be selected or not based upon the desire of the surgeon, for increased number of direct compressions surface with suture strands versus those anchor devices lacking the rotatable ring. Additionally, the suture anchor device may be provided using plastic instead of metal, its radio opaque quality, minimal MRI interference and other factors. It is economically superior to the Huxel patent due to its optional elements and its durability, which most surgeons would find beneficial to their patients, with multiple benefits and advantages over prior art suture anchors.

II. SUMMARY OF THE INVENTION

Suture anchors are commonly used in orthopedic surgical procedures as a means to secure soft tissues to bone. Knotted suture anchors often comprise a bone anchor which is placed in a drilled cavity within a bone at a particular location with a soft tissue connecting to the bone anchor by way of a suture tied and secured to the soft tissue and tied off against the installed bone anchor. Some bone anchor devices require a knot to be tied in the suture, while others are "knotless" suture anchors, meaning the sutures are held within the bone anchor without the need to tie a knot in the suture to provide the secure connection. As noted in the prior art disclosed above, there are several different suture anchors employing a knotless attachment to the bone anchor and many anchors employing knotted sutures.

The suture anchor of the prior art requires the installation of the bone anchor, the attachment of a suture to the soft tissue and the tightening of the suture and attached soft tissue drawn towards the bone anchor. The suture is them secured within the bone anchor at a desired tension, whether securing by knot or knotlessly, securing the soft tissue to the bone anchor, or at least in that general direction. Often, the soft tissue as drawn towards the bone anchor will result in the soft tissue suture having an angular tension alignment with the bone anchor. This can result in misalignment of the soft tissue or an inappropriate level of stress placed upon the suture to soft tissue connection, which may ultimately result in a tearing or weakening of the connected soft tissue due to the bone anchor lacking an ability to rotate towards the direct line of tension towards the suture attaching the soft tissue relieving this unnecessary stress.

Most prior art sutures anchors are characterized by the suture being secured towards the distal end of the anchor and in some cases the suture traverses through the length of the anchor and out the distal end, with the suture running adjacent to the bone and outer surface of the suture anchor. These methods for securing the suture can lead to loosening of the suture due to bone cutting suture in hard bone surfaces and increased length of the suture being secured that has potential for increased elongation of the suture. This can result in a loose failed repair of soft tissue to bone, and often fine tensioning loss, wherein the repair of the prior art suture anchor repair may be too tight or too loose for optimal healing of soft tissue to bone. Top locking suture anchors are defined as having the suture enter the top of the anchor with the locking mechanism also located at the top of the anchor. However, the prior art top locking anchors lack the ability to rotate towards the direct line of tensioning towards the suture attaching the soft tissue relieving unnecessary stress from a lack of mobility.

Therefore, if the tension of the suture were adjustable in rotation in a straight line with the soft tissue connection, before, during and subsequent to the attachment of the suture within the bone anchor, this potential unnecessary stress could be reduced or entirely eliminated. It is therefore the objective of the present rotatable knotless or knotted suture anchor to provide the suture anchor with the ability to rotate on an axis prior to, during and subsequent to the attachment of a suture attaching a soft tissue to the bone anchor. It also provides the suture attachment to connect to the anchor with or without a knot in the suture and with the ability to attach and detach the suture on more than one occasion during a surgical procedure where multiple bone anchors are used or where multiple soft tissues are being attached to multiple bone anchors. An installation tool for the suture anchor is also provided and disclosed.

I. DESCRIPTION OF THE DRAWINGS

The following drawings are submitted with this utility patent application.

FIG. 1 is a side cross section of a first embodiment of a top locking rotatable suture anchor in a closed position.

FIG. 2 is a side cross section of the first embodiment of the rotatable suture anchor in an open position with the eyelet pin rotated to view through transverse suture passage.

FIG. 3 is an exploded perspective view of the first embodiment of the rotatable suture anchor indicating assembly along a longitudinal axis.

FIG. 6 is a side cross section of the second embodiment of the top locking rotatable suture anchor in a closed position.

FIG. 7 is a side cross section of a second embodiment of the rotatable suture anchor in an open position.

FIG. 11 is a side cross section of the first embodiment of the rotatable suture anchor in an open position with the eyelet pin rotated to view a cross section of the transverse suture passage, the eyelet pin rotated ninety degrees from that shown in FIG. 2.

FIG. 12 is a side view of an embodiment of the suture anchor with a threaded elevated ridge on the outer surface as the bone securing means and an eyelet expansion containing a recessed portion adjacent to the transverse passage on the eyelet pin.

FIG. 16 is an isolated view of an embodiment of a frangible nose ring.

FIG. 17 is an isolated view of another embodiment of a frangible nose ring.

FIG. 19 is a cross sectional view of the first embodiment of the suture anchor in a closed position demonstrating the securing of a suture.

FIG. 20 is a cross sectional view of the second embodiment of the suture anchor in a closed position demonstrating the securing of a suture.

FIG. 21 is an upper perspective view of the connection components between the tip of the delivery tool and the suture anchor exposing the tool portion of the eyelet pin and ring slot.

FIG. 23 is a cross sectional view of a third embodiment of the top locking suture anchor in a closed position, having only a suture anchor body and an eyelet pin.

FIG. 24 is a cross sectional view of the third embodiment of the suture anchor in an open position, having only a suture anchor body and an eyelet pin.

FIG. 26 is a cross sectional view of a fourth embodiment of the suture anchor in a closed position, having a suture anchor body, a rotatable ring and an eyelet pin.

FIG. 27 is a cross sectional view of the fourth embodiment of the suture anchor in an open position, having a suture anchor body, a rotatable ring and an eyelet pin.

FIG. 28 is an exploded view of the fourth embodiment of the top locking suture anchor demonstrating the assembly of the suture anchor body, the rotatable ring and the eyelet pin along a longitudinal axis.

IV. DESCRIPTION OF THE PREFERRED EMBODIMENT

Figure 4:
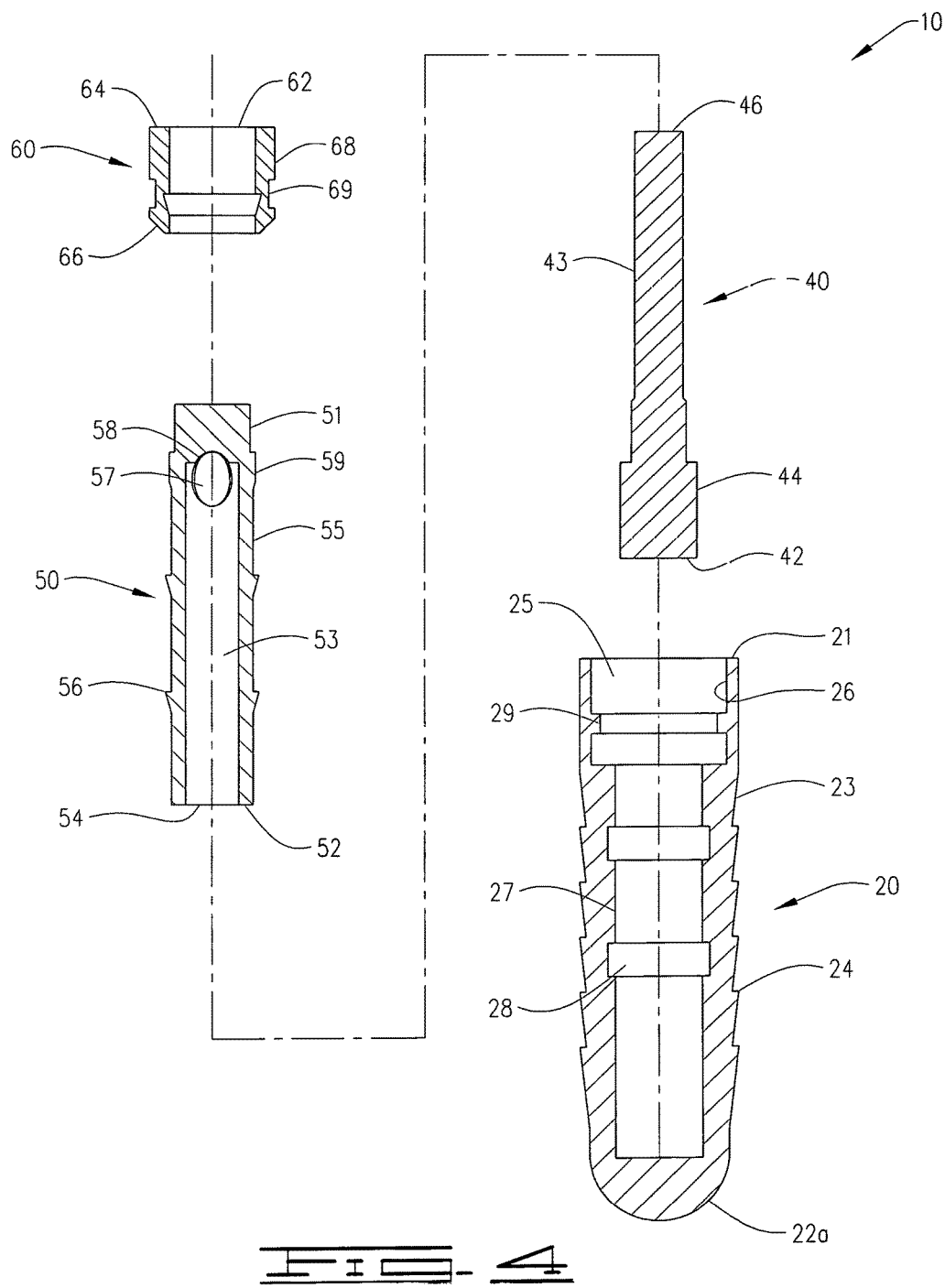
FIG. 4 is side cross sectional exploded view of the first embodiment of the rotatable suture anchor with assembly along a longitudinal axis.
Figure 5:
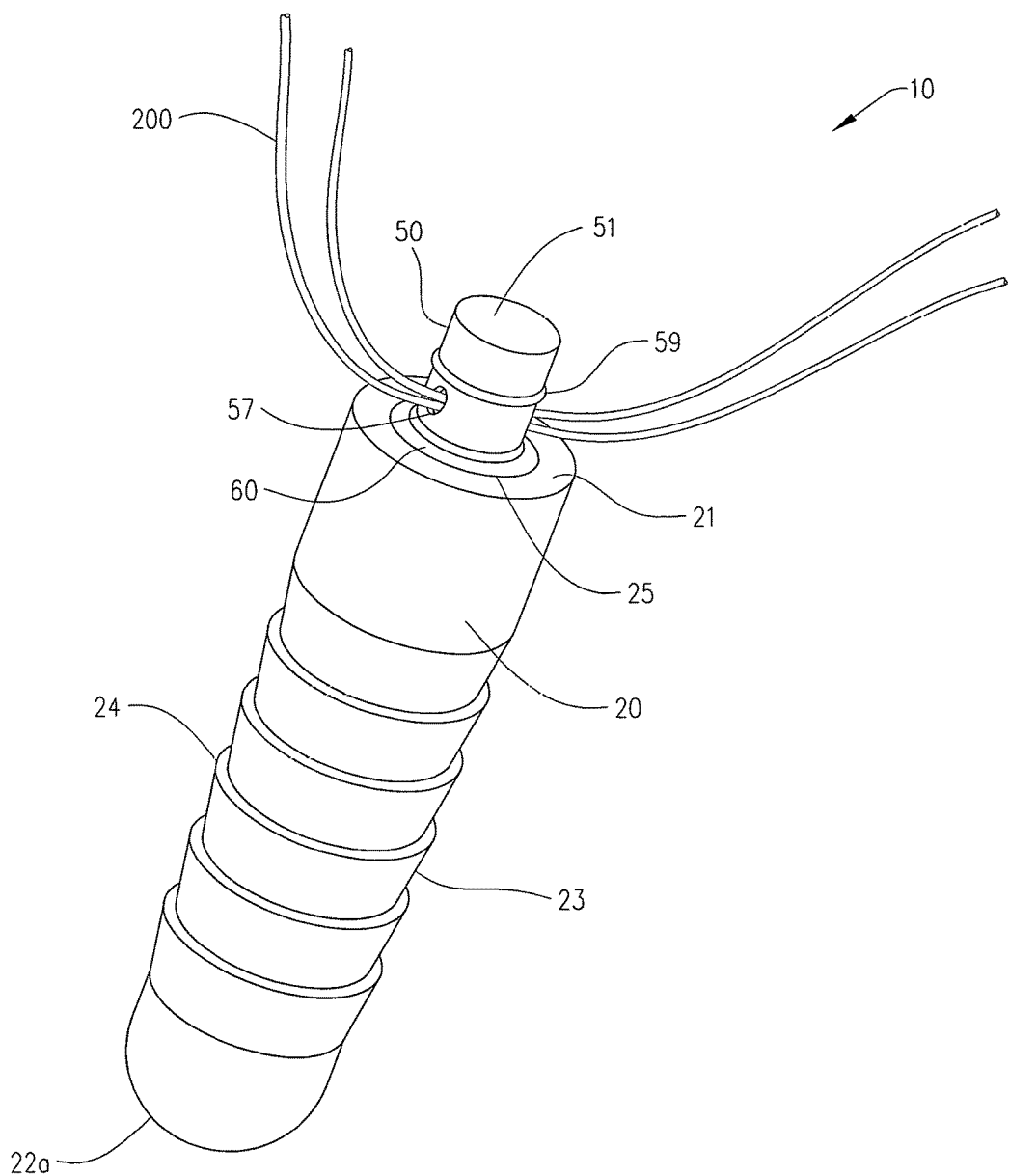
FIG. 5 is an upper perspective view of the first embodiment of the rotatable suture anchor in the open position including two sutures threaded through the transverse suture passage in the eyelet pin.

A rotatable top locking suture anchor device 10, shown in several embodiments of FIGS. 1-28 and as disclosed within the specification and claims, provide the suture anchor 10 for use in orthopedic surgical procedures to attach soft tissue to a bone using one or more sutures 200, provides the suture anchor device 10 for adjustment of an angle of tension and rotation subsequent to installation with options for knotted or knotless use.

In a first embodiment, disclosed in FIGS. 1-5, 9-13 and 19, the top locking suture anchor device 10 comprises an anchor body 20 defining an upper end 21 and a lower end 22a defining a longitudinal axis between the upper and lower ends, an outer surface 23 extending a plurality of bone securing projections 24, the anchor body 20 further defining a inner longitudinal chamber 25 along the longitudinal axis having an upper chamber expansion 26 providing an upper ring lock extension 29, and an inner wall 27 including circumferential inner locking grooves 28 and a bottom 30a. In another embodiment, FIGS. 9 and 10, the anchor body 20 defines a lower chamber opening 22b within which is inserted a nosepiece 30b defining a lower tip 32 extending below the anchor body 20, the nosepiece 30b also providing a upper plug end 34 inserted within the lower chamber opening 22b to seal the anchor body 20 from below. This embodiment of may also provide an upper pin orifice 36.

The suture anchor device 10 further provides a central pin 40, FIGS. 1-4, 11 and 19, defining a base 42 set within the bottom 30a of the inner longitudinal chamber 25, the central pin 40 further extending an upright cylindrical slide shaft 43 having an expanded lower end 44 and an upper end 46. In the embodiment of the anchor body 20 having the nosepiece 30b, the base 42 of the central pin 40 is installed within the upper pin orifice 36 of the nosepiece 30b, FIG. 10. or may incorporate the base 42 of the central pin 40 within the nosepiece 30b, FIG. 9. The area within the inner longitudinal chamber 25 between the inner wall 27 of the anchor body 20 and the upright cylindrical slide shaft of the installed central pin 40 defines an annular space 49.

An eyelet pin 50 is included within the first embodiment, FIGS. 1-5, 11-13 and 19, with the eyelet pin 50 defining a proximal end 51 and a distal end 52, a lower inner bore 53 defining a lower bore opening 54 at the distal end 52, an outer surface 55 defining a plurality of pin lock extensions 56, with the proximal end 51 forming a transverse passage 57 within which at least one suture 200 may be passed, the transverse passage 57 including a roof 58, with the proximal end 51 extending a radial ring lock expansion 59. The lower inner bore 53 of the eyelet pin 50 inserts and slidably engages the cylindrical slide shaft 43 of the central pin 40 within the annular space 49, being raised and lowered upon the cylindrical slide shaft 43, with the one or more of the plurality of pin lock extensions 56 selectively engaging one or more respective circumferential inner locking grooves 28 of the inner wall 27 within the anchor body 20. The eyelet pin 50 includes a open position, FIGS. 2 and 5, wherein the at least one suture 200 may be freely passed through the transverse passage 57 of the eyelet pin 50, and closed position, FIGS. 1, 13 and 19, wherein the at least one suture 200 is secured within the transverse passage 57, held without requiring the suture 200 to be tied or knotted.

The first embodiment defines a rotatable ring 60 installed within the upper end 21 of the anchor body 20 and fitted between the proximal end 51 of the eyelet pin 50 and the inner longitudinal channel 25 within the upper chamber expansion 26, FIGS. 1-5, 11, 13 and 19. The rotatable ring 60 forms an inner opening 62 suitable to receive the proximal end 51 of the eyelet pin 50 with the ring lock expansion 59 moving within the inner opening 62, the rotatable ring further defining an upper end 64, a tapered lower margin 66, and an outer surface 68 forming a ring lock groove 69. As the rotatable ring 60 is inserted within the upper chamber expansion 26, the ring lock extension 29 within the upper chamber expansion 26 is secured within the ring lock groove 69 of the rotatable ring 60, FIGS. 1, 11 and 19, retaining the rotatable ring 60 within the upper chamber expansion 26 while allowing the proximal end 51 of the eyelet pin 50 to be raised and lowered within the inner opening 62 without impairment or movement of the rotatable ring 60 from its secure placement within the upper chamber expansion 26. The eyelet pin 50 remains rotatable within the inner longitudinal chamber 25 as does the rotatable ring 60, regardless of the eyelet pin 50 being in the open or closed position.

The bone securing projections 24 on the outer surface 23 of the anchor body 20 may be provided as, but not limited to partially or fully circumferential barbed rings, FIGS. 1-5, 9-11 and 13, where the anchor body 20 is pushed into a hole in a bone drilled prior to installation, or as an axially thread, FIG. 12, which would require the anchor body 20 to be screwed into the hole in a bone. It is the purpose of the bone securing projections 24 to retain the anchor body 20 in the bone to which the soft tissue is subsequently attached by the at least one suture 200 captured within the suture anchor device 20. The pin lock extensions 56 of the eyelet pin 50 may be provided as upward angled barbed rings, shown in FIGS. 1-4 or other elevated extensions located on the outer surface 55 of the eyelet pin 50. As shown in FIG. 1, which is a closed position of the first embodiment, at least two pin lock extensions 56 engage at least two respective circumferential inner locking grooves 28 to retain the eyelet pin 50 upon the central pin 40 within the inner longitudinal chamber 25, "locking" the eyelet pin 50 into the closed position and securing the at least one suture 200 within the transverse passage 57, requiring intentional removal of the eyelet pin 50 for disengagement into the open position. In the open position, FIG. 2, at least one pin lock extension 56 engages at least one respective inner locking groove 28 to hold the eyelet pin 50 upon the central pin 40 within the inner longitudinal chamber 25, thereby allowing for movement of the suture 200 contained within the transverse passage 57 until such time as the eyelet pin 50 is pushed down and the suture anchor device 10 is in the closed position of FIG. 1.

In the closed position, FIG. 19, the securing of the at least one suture 200 is shown in this first embodiment, with the at least one suture 200 compressed between the inner opening 62 of the rotatable ring 60 and the ring lock expansion 59, retained against the roof 58 of the transverse passage 57 as the at least one suture 200 extends beyond both sides of the eyelet pin 50 and between the upper end 64 of the rotating ring 60 and the proximal end 51 of the eyelet pin 50. Depending on the size and material of the suture, the closed position may still allow the suture 200 to slide through the transverse passage 57 while in the closed position, which would depend on the relative size of the transverse passage 57 compared to the diameter of the suture 200. Therefore, the sutures 200 may be secured within the transverse passage 57 in a closed position and be a knotless connection, or may still slide through the transverse passage 57 in a closed position, which would require the sutures 200 to be tied or knotted by the surgeon.

Figure 13:
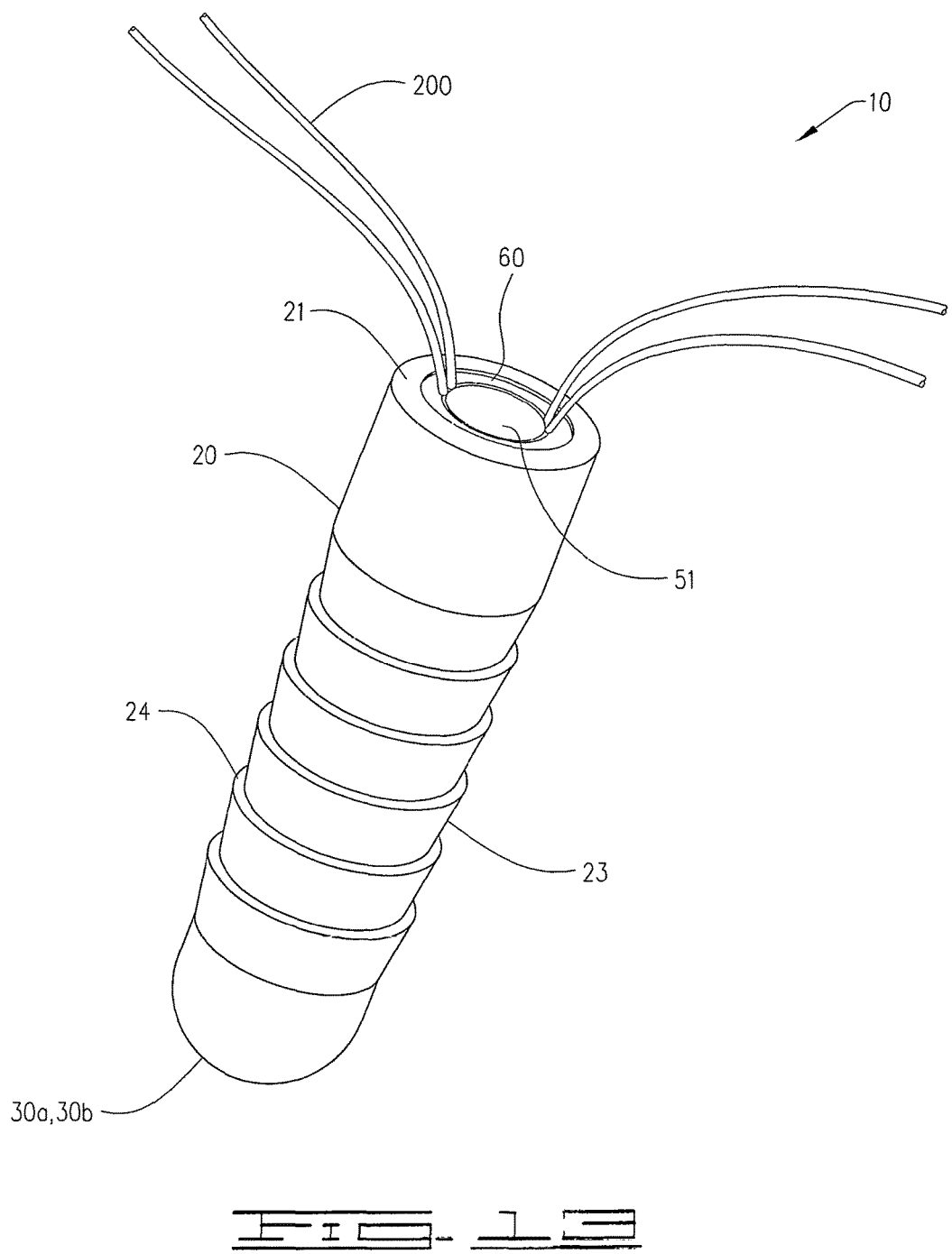
FIG. 13 is a view of FIG. 5 in a closed position.

As shown in FIGS. 13 and 19, even in a closed position, the rotatable ring 60 and eyelet pin 50 are intended to be rotatable up to 360 degrees when securing at least one installed suture 200 within the inner longitudinal chamber 25 of the anchor body 20, the eyelet pin 50 being rotatable on the central pin 40 and the rotatable ring 60 further rotatable within the upper chamber expansion 26, regardless of the engagement of the ring lock groove 69 to ring lock extension 29, and regardless of the engagement of the at least one pin lock extensions 56 within the respective at least one inner locking groove 28.

FIG. 19 illustrates that the transverse passage 57 and the inner bore 53 of the eyelet pin 50 may intersect, allowing partial entry of the upper end 46 of the central pin 40 to intrude into the transverse passage 57 when the suture anchor device 10 is in a closed position. In certain versions of the first embodiment, the upper end 46 may be capable of pinning the at least one suture 200 against the roof 58 of the transverse passage 57, providing a further securing feature of the suture anchor device 10 to retain the suture 200 within the suture anchor device 10.

A second embodiment of the top locking suture anchor device 10, shown in FIGS. 6-8 and 20, comprises essentially the same components as the first embodiment, except for an absence of the rotatable ring 60 and lack of some of the rotatable ring accommodations in other elements. The anchor body 20 provides an upper end 21, a lower end 22a with an outer surface 23 extending a plurality of bone securing projections 24, an inner longitudinal chamber 25 defining an upper chamber expansion 26 and an inner wall 27 containing one or more circumferential inner locking grooves 28. The central pin 40 includes the base 42, the cylindrical slide shaft 43, a lower end 44, FIGS. 6 and 7 and the upper end 46. The same annular space 49 is defined between the central pin 40 the inner wall 27 of the inner longitudinal chamber 25 of the anchor body 20. The eyelet pin 50 defines a proximal end 51 and a distal end 52, an inner bore 53 defining a lower bore opening 54 into which the upper end 46 of the central pin 40 inserts and forms a sliding engagement between the cylindrical slide shaft 43 and the inner bore 53, with the eyelet pin 50 further defining an outer surface 55 extending a plurality of pin lock extensions 56, and the proximal end 51 containing the transverse passage 57 defining a roof 58. A ring lock extension 29 is still present in the second embodiment, even though there is no rotating ring 60, the ring lock extension 29 serving as a suture compression feature for the second embodiment. It may be suitable to reference this element as something other than a ring lock extension 29, but since it is a common feature of both the first and second embodiments, the common nomenclature of this feature would be appropriate.

FIG. 7 demonstrates the second embodiment of the suture anchor device 10 in an open position, while FIG. 6 demonstrates the second embodiment in the closed position, similarly seen in FIG. 20 containing at least one suture 200. FIGS. 6 and 7 show the second embodiment with the solid anchor body 20. FIG. 20 shows the anchor body 20 alternatively including a lower chamber opening 22b with a nosepiece 30b of FIG. 10, wherein the nosepiece 30b includes a lower tip 32, upper plug end 34 and an upper pin orifice 36 within which the base 42 of the central pin 40 is inserted. The second embodiment may further contain the nosepiece 30b of FIG. 9 which demonstrates the central pin 40 integrated with the nosepiece 30b.

Figure 8:
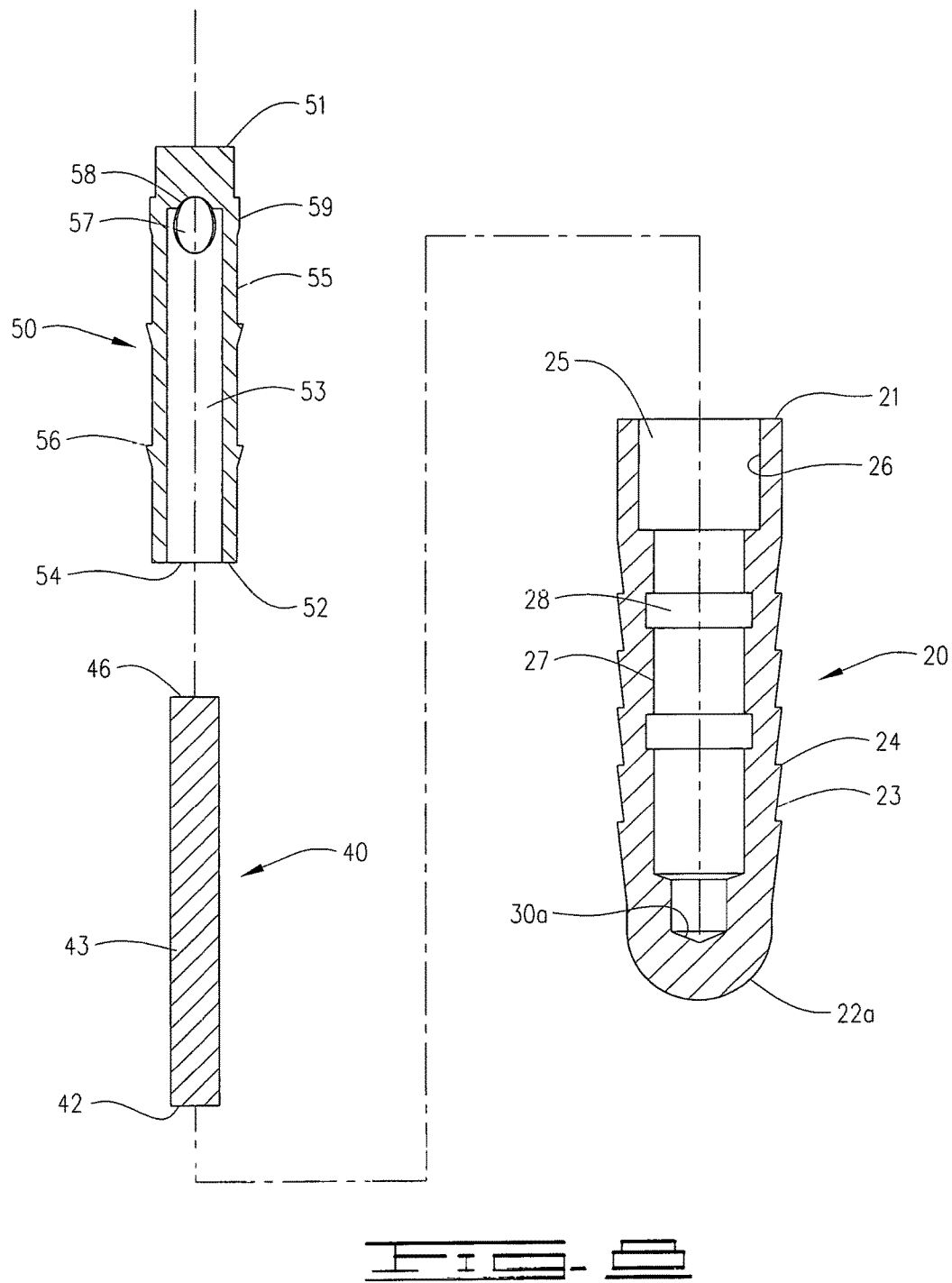
FIG. 8 is a side cross section exploded view of the second embodiment of the rotatable suture anchor showing assembly along a longitudinal axis.
Figure 9:
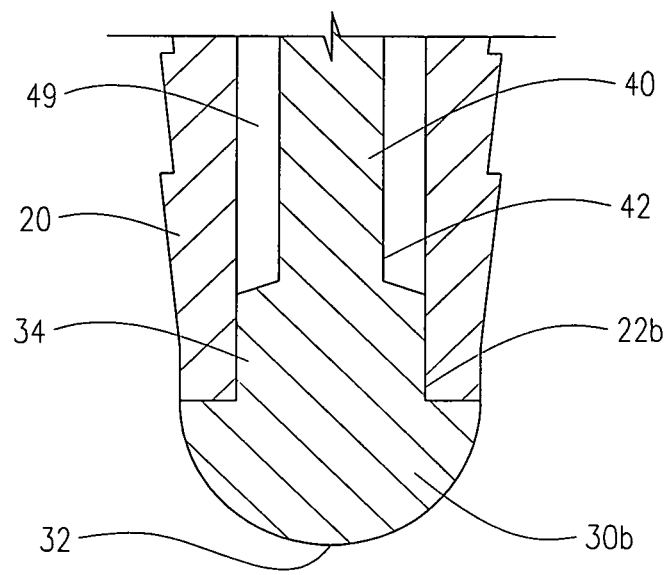
FIG. 9 is an isolated cross sectional view of an embodiment of an anchor nosepiece with an integrated a lower end of the central pin.
Figure 10:
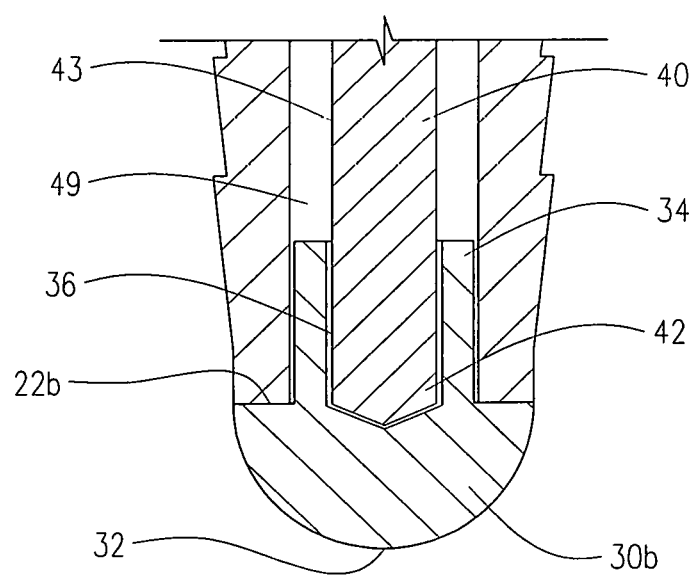
FIG. 10 is an isolated cross sectional view of an embodiment of an anchor nosepiece with a central pin cavity securing the lower end of the central pin.

The bone securing projections 24 on the outer surface 23 of the anchor body 20 of the second embodiment may be provided as, but not limited to fully circumferential or partially circumferential barbed rings, FIGS. 6-8, where the anchor body 20 is pushed into a hole in a bone drilled prior to installation, or as an axially thread, FIG. 12, which would require the anchor body 20 to be screwed into the hole in a bone. It is the purpose-of the bone securing projections 24 to retain the anchor body 20 in the bone to which the soft tissue is subsequently attached by the at least one suture 200 captured within the suture anchor device 10. The pin lock extensions 56 of the eyelet pin 50 may be provided as upward angled barbed rings, shown in FIGS. 6-8 or other elevated extensions located on the outer surface 55 of the eyelet pin 50. As shown in FIG. 6, which is a closed position of the second embodiment, at least two pin lock extensions 56 engage at least two respective circumferential inner locking grooves 28 to retain the eyelet pin 50 upon the central pin 40 within the inner longitudinal chamber 25, retaining the eyelet pin 50 into the closed position and securing the at least one suture 200 within the transverse passage 57, requiring intentional removal of the eyelet pin 50 for disengagement into an open position. In the open position, FIG. 7, at least one pin lock extension 56 engages at least one respective inner locking groove 28 to hold the eyelet pin 50 upon the central pin 40 within the inner longitudinal passage 25, thereby allowing for movement of the suture 200 contained within the transverse passage 57 until such time as the eyelet pin 50 is pushed down and the suture anchor device 10 is in the closed position of FIG. 7.

In the closed position, FIG. 20, the securing of the at least one suture 200 is shown in this second embodiment, with the at least one suture 200 compressed between the ring lock expansion 59 of the eyelet pin 50 and the upper chamber expansion 26 of the anchor body 20 as the at least one suture 200 is threaded through the transverse passage 57 of the eyelet pin 50, with the at least one suture 200 retained against the roof 58 of the transverse passage 57 as the at least one suture 200 extends from the transverse passage 57 on both sides of the eyelet pin 50 and outside the proximal end 51 of the eyelet pin 50. Depending on the size and material of the sutures 200, the closed position may still allow the suture 200 to slide through the transverse passage 57 while in the closed position, which would depend on the relative size of the transverse passage 57 compared to the diameter of the suture 200. Therefore, the sutures 200 may be secured within the transverse passage 57 in a closed position and be a knotless connection, or may still slide through the transverse passage 57 in a closed position, which would require the sutures to be tied or knotted by the surgeon.

As shown in FIGS. 6 and 20, even in a closed position, the eyelet pin 50 is intended to be rotatable up to 360 degrees along the longitudinal axis when securing at least one installed suture 200 within the inner longitudinal chamber 25 of the anchor body 20, the eyelet pin 50 being rotatable on the central pin 40 regardless of the engagement of the eyelet pin 50 within the upper chamber expansion 26, and regardless of the engagement of the at least one pin lock extensions 56 within the respective at least one inner locking groove 28.

FIG. 20 further illustrates that the transverse passage 57 and the inner bore 53 of the eyelet pin 50 may intersect, allowing partial entry of the upper end 46 of the central pin 40 to intrude into the transverse passage 57 when the suture anchor device 10 is in a closed position. In certain versions of the second embodiment, the upper end 46 may be capable of pinning the at least one suture 200 against the roof 58 of the transverse passage 57, providing a further securing feature of the suture anchor device 10 to retain the suture 200 within the suture anchor device 10.

Figure 25:
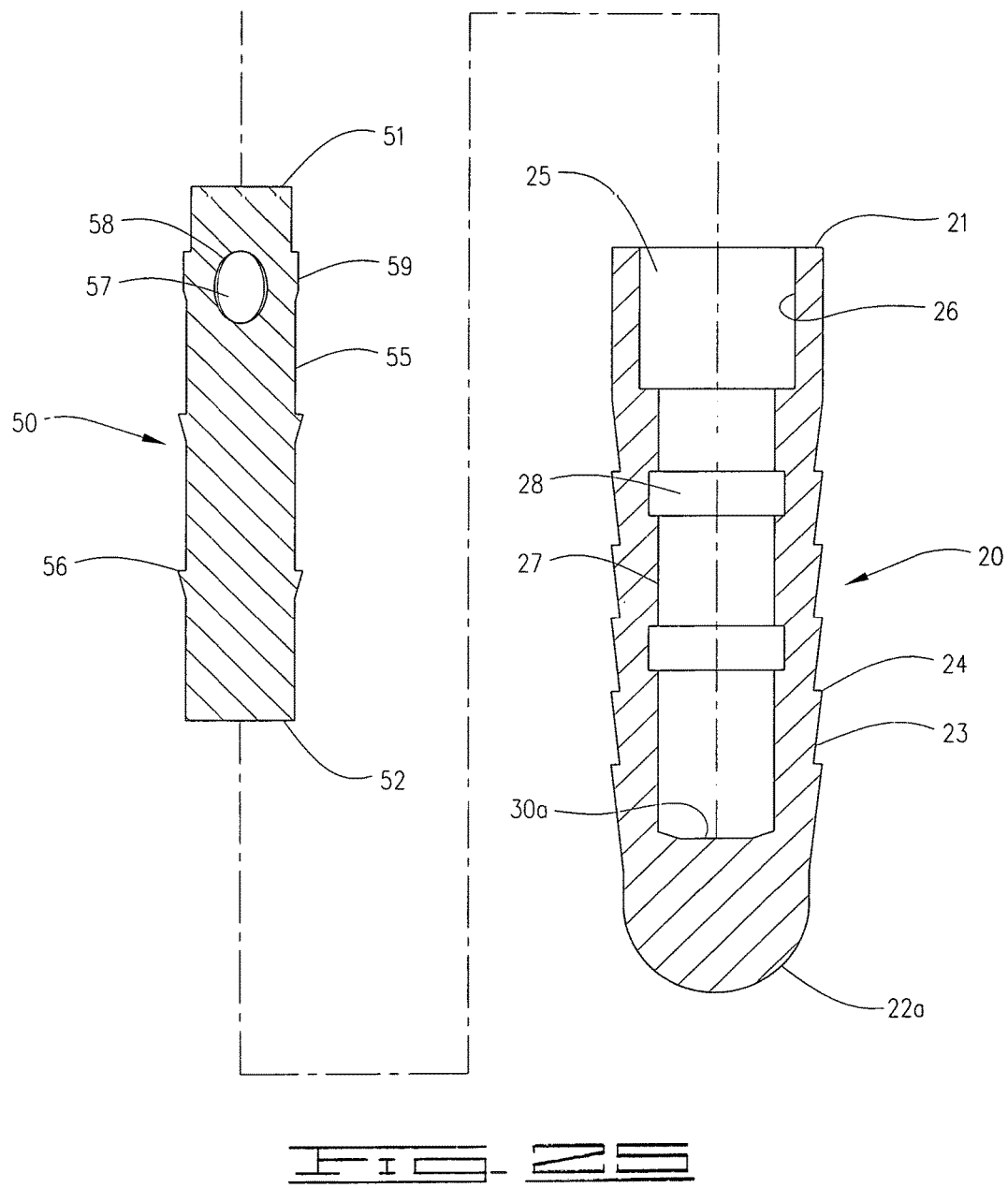
FIG. 25 is an exploded view of the third embodiment of the suture anchor demonstrating the assembly of the suture anchor body and an eyelet pin along a longitudinal axis.

FIGS. 23-25 of the drawing figures illustrates a third embodiment of the top locking suture anchor device 10 providing the most simple construction, employing only an anchor body 20 and an eyelet pin 50. The anchor body 20 can be the same as disclosed in the first and second embodiment, comprising an upper end 21, lower end 22a, outer surface 23 including bone securing projections 24, an inner longitudinal chamber 25 defining an upper chamber expansion 26, an inner wall 27 providing at least one inner locking groove 28, and a bottom 30a. FIGS. 23 and 24 illustrate two circumferential inner locking grooves 28. Once again, the bone secure projections 24 are intended to gain purchase within the bone where the suture anchor device 10 is installed, and may be provided as fully circumferential or partially circumferential barbed rings, where the anchor body 20 is pushed into a hole in a bone drilled prior to installation, or as an axially thread, which would require the anchor body 20 to be screwed into the hole in a bone. It is the purpose of the bone securing projections 24 to retain the anchor body 20 in the bone to which the soft tissue is subsequently attached by the at least one suture 200 captured within the suture anchor device 10. The anchor body 20 may alternatively define a lower chamber opening 22b, with a nose piece 30b defining a lower tip 32 and an upper plug end 34 and without an upper pin orifice, 36, since there is no central pin 40 in the third embodiment. The third embodiment of the eyelet pin 50 may be a solid component defining a proximal end 51, a distal end 52, an outer surface 55 defining at least one pin lock extension 56, a transverse passage 57 which may define a roof 58, the transverse passage 57 traversing the proximal end 51 of the eyelet pin 50, and alternatively a ring lock expansion 59 or an eyelet expansion 59a, FIG. 12, with a recessed portion 59b. Unlike the first two embodiment, the eyelet pin 50 does not require an inner bore 53 with a lower bore opening 54, because there is no central pin 40 with which to integrate or interact. The eyelet pin 50 of the third embodiment may thus be more economically manufactured along with a simple anchor body 20, for the most cost effective embodiment of any of the suture anchor devices 10 disclosed herein.

In a third embodiment, the pin lock extensions 56 of the eyelet pin 50 may be provided as upward angled barbed rings, shown in FIGS. 23-25, or other elevated extensions located on the outer surface 55 of the eyelet pin 50. As shown in FIG. 23, which is a closed position of the third embodiment, at least two pin lock extensions 56 engage at least two respective circumferential inner locking grooves 28 to retain the eyelet pin 50 upon the central pin 40 within the inner longitudinal chamber 25, retaining the eyelet pin 50 into the closed position, which may securing the at least one suture 200 within the transverse passage 57, requiring intentional removal of the eyelet pin 50 for disengagement into an open position. Depending on the size and material of the sutures 200, the closed position may still allow the sutures 200 to slide through the transverse passage 57 while in the closed position, which would depend on the relative size of the transverse passage 57 compared to the diameter of the sutures 200. Therefore, the sutures may be secured within the transverse passage 57 in a closed position and be a knotless connection, or may still slide through the transverse passage 57 in a closed position, which would require the suture to be tied or knotted by the surgeon.

FIGS. 26-28 of the drawing figures illustrates a fourth embodiment of the top locking suture anchor device 10 providing somewhat of a hybrid construction between the first and third embodiments, employing an anchor body 20, a rotatable ring 60 and an eyelet pin 50. The anchor body 20 can be the same as disclosed in the first, second and third embodiment, comprising an upper end 21, lower end 22a, outer surface 23 including bone securing projections 24, an inner longitudinal chamber 25 defining an upper chamber expansion 26, an inner wall 27 providing at least one inner locking groove 28, and a bottom 30a. FIGS. 26 and 27 illustrate two circumferential inner locking grooves 28. Once again, the bone secure projections 24 are intended to gain purchase within the bone where the suture anchor device 10 is installed, and may be provided as fully or partially circumferential barbed rings, where the anchor body 20 is pushed into a hole in a bone drilled prior to installation, or as an axially thread, which would require the anchor body 20 to be screwed into the hole in a bone. It is the purpose of the bone securing projections 24 to retain the anchor body 20 in the bone to which the soft tissue is subsequently attached by the at least one suture 200 captured within the suture anchor device 10. The anchor body 20 may alternatively define a lower chamber opening 22b, with a nose piece 30b defining a lower tip 32 and an upper plug end 34 and without an upper pin orifice, 36, since there is no central pin 40 in the third embodiment. The fourth embodiment of the eyelet pin 50 may be a solid component defining a proximal end 51, a distal end 52, an outer surface 55 defining at least one pin lock extension 56, a transverse passage 57 which may define a roof 58, the transverse passage 57 traversing the proximal end 51 of the eyelet pin 50, and alternatively a ring lock expansion 59 or an eyelet expansion 59a, with a recessed portion 59b. The eyelet pin 50 does not require an inner bore 53 with a lower bore opening 54, because there is no central pin 40 with which to integrate or interact. The boreless eyelet pin 50 of the fourth embodiment may still be more economically manufactured for the most cost effective embodiment of any of the suture anchor devices 10 disclosed herein. In a fourth embodiment, the pin lock extensions 56 of the eyelet pin 50 may be provided as upward angled barbed rings, shown in FIGS. 26-28, or other elevated extensions located on the outer surface 55 of the eyelet pin 50.

As shown in FIG. 26, which is a closed position of the fourth embodiment, at least two pin lock extensions 56 engage at least two respective circumferential inner locking grooves 28 to retain the eyelet pin 50 upon the central pin 40 within the inner longitudinal chamber 25, retaining the eyelet pin 50 into the closed position, which may securing the at least one suture 200 within the transverse passage 57, requiring intentional removal of the eyelet pin 50 for disengagement into an open position. Depending on the size and material of the sutures 200, the closed position may still allow the sutures 200 to slide through the transverse passage 57 while in the closed position, which would depend on the relative size of the transverse passage 57 compared to the diameter of the sutures 200. Therefore, the sutures may be secured within the transverse passage 57 in a closed position and be a knotless connection, of may still slide through the transverse passage 57 in a closed position, which would require the suture to be tied or knotted by the surgeon.

The fourth embodiment, just like the first embodiment, defines a rotatable ring 60 installed within the upper end 21 of the anchor body 20 and fitted between the proximal end 51 of the eyelet pin 50 and the inner longitudinal channel 25 within the upper chamber expansion 26, FIGS. 26-28. The rotatable ring 60 forms a inner opening 62 suitable to receive the proximal end 51 of the eyelet pin 50 with the ring lock expansion 59 moving within the inner opening 62, the rotatable ring further defining an upper end 64, a tapered lower margin 66, and an outer surface 68 forming a ring lock groove 69. As the rotatable ring 60 is inserted within the upper chamber expansion 26, the ring lock extension 29 within the upper chamber expansion 26 is secured within the ring lock groove 69 of the rotatable ring 60, FIGS. 26-27, retaining the rotatable ring 60 within the upper chamber expansion 26 while allowing the proximal end 51 of the eyelet pin 50 to be raised and lowered within the inner opening 62 without impairment or movement of the rotatable ring 60 from its secure placement within the upper chamber expansion 26. The eyelet pin 50 remains rotatable within the inner longitudinal chamber 25 as does the rotatable ring 60, regardless of the eyelet pin 50 being in the open or closed position.

In the open position, FIGS. 2, 5, 7,11, 24 and 27, at least one pin lock extension 56 engages at least one respective inner locking groove 28 to hold the eyelet pin 50 upon the central pin 40 within the inner longitudinal passage 25, thereby allowing for movement of the suture 200 contained within the transverse passage 57 until such time as the eyelet pin 50 is pushed down and the suture anchor device 10 is in the closed position of FIG. 7.

The eyelet expansion 59a, FIG. 12, with a recessed portion 59b are alternative designs of the eyelet pin 50. These may be chosen in all four embodiments of the suture anchor device 10. The ring lock expansion 59 is an undefined shaped expansion selected in the first embodiment wherein this ring lock expansion 59 installs within the rotatable ring 60. The sizes and shaped of the inner opening 62 of the rotatable ring 60 and the ring lock expansion 59 may be provided an a variety of relative engagement depending on the type suture security desired by the surgeon—as would be indicated in a knotless, knotted or tied selection for the suture attachment. In the second and third embodiments, for example, the eyelet expansion 59a with the recess portion might alternatively be chosen wherein the eyelet expansion 59a is engaged within the ring lock extension 29 of the anchor body 20 as one of the securing features to retain sutures 200 connecting within the transverse passage 57, with the eyelet expansion 59a providing compression to the emanating sutures 200 for a chosen non-sliding knotless engagement of the suture while the suture anchor device is in a closed position. Alternatively, the eyelet expansion 59a includes the recess portion 59b located at the end of the transverse passage 57 on one or both sides of the eyelet pin 50, with the recessed portion 59b being a reduced diameter than the eyelet expansion 59a, allowing the sutures to pass through the recessed portion 59b without having to pass over or around the eyelet expansion 59a where a knotted or tied suture is preferred and where a sliding engagement between the suture 200 and the suture anchor device 10 in a closed position is preferred over a non-sliding engagement, wherein a slidable knotless deployment the sutures may be preferred to allow the surgeon, who may choose to maintain ability to finely adjust the tension of the suture.

While the rotatable suture anchor device 10 may be installed and utilized in any appropriate surgical manner by those skilled in the field of orthopedic surgery, a preferable means of delivery of the rotatable suture anchor device, a compatible delivery tool 100, as shown and disclosed in FIGS. 14-15, 18 and 21-22, is recommended and suited for the preferred installation of the rotatable suture anchor device 10, integrating with the suture anchor device 10. This delivery tool 100 is especially suitable for an embodiment of the suture anchor device 100 wherein the rotatable ring 60 of the first and fourth embodiments is supplied as a frangible component of a frangible ring connector 150, shown in FIGS. 14-18 of the drawing illustrations.

Figure 14:
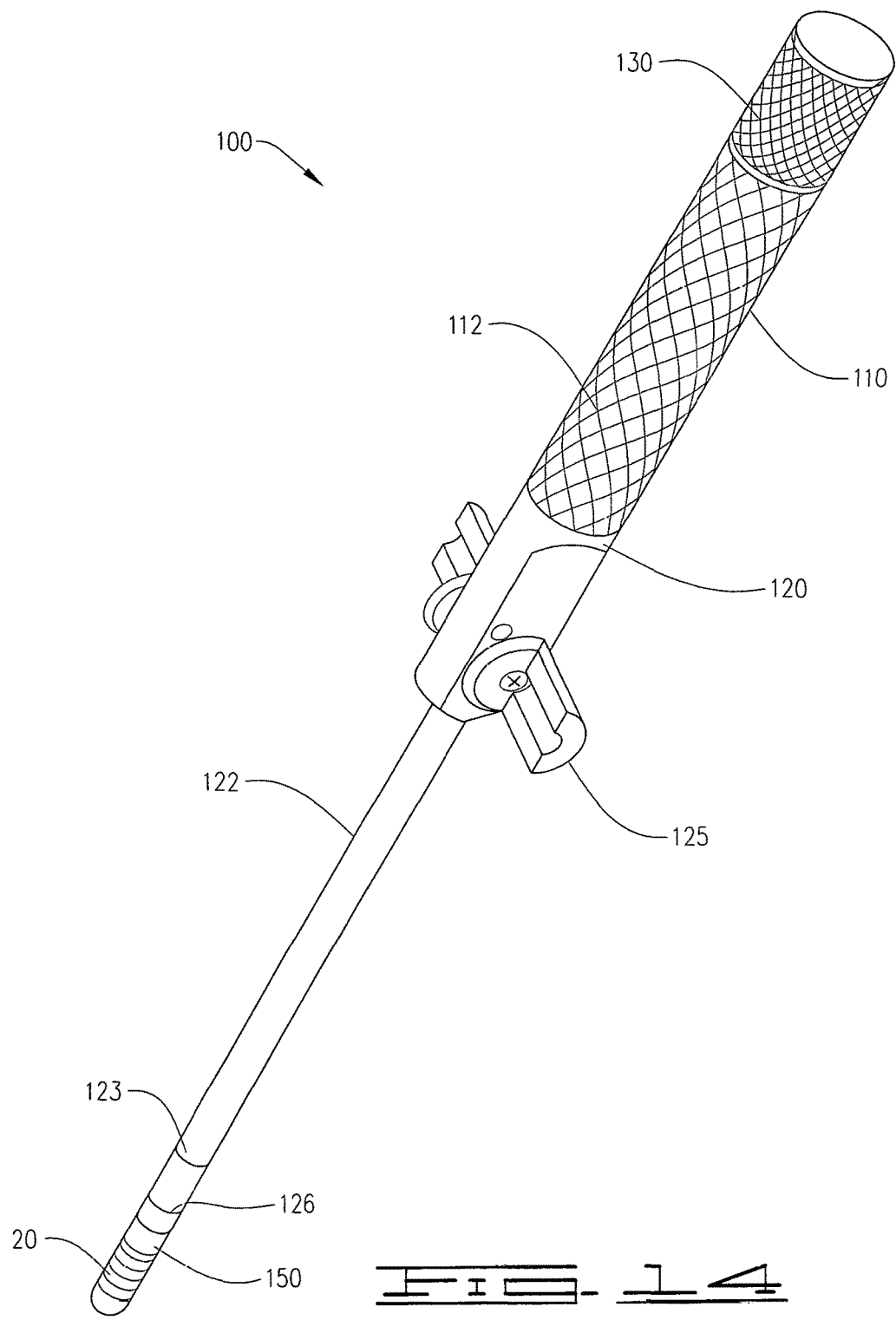
FIG. 14 is a side view of the delivery tool and a suture anchor connected to a frangible nose ring.
Figure 15:
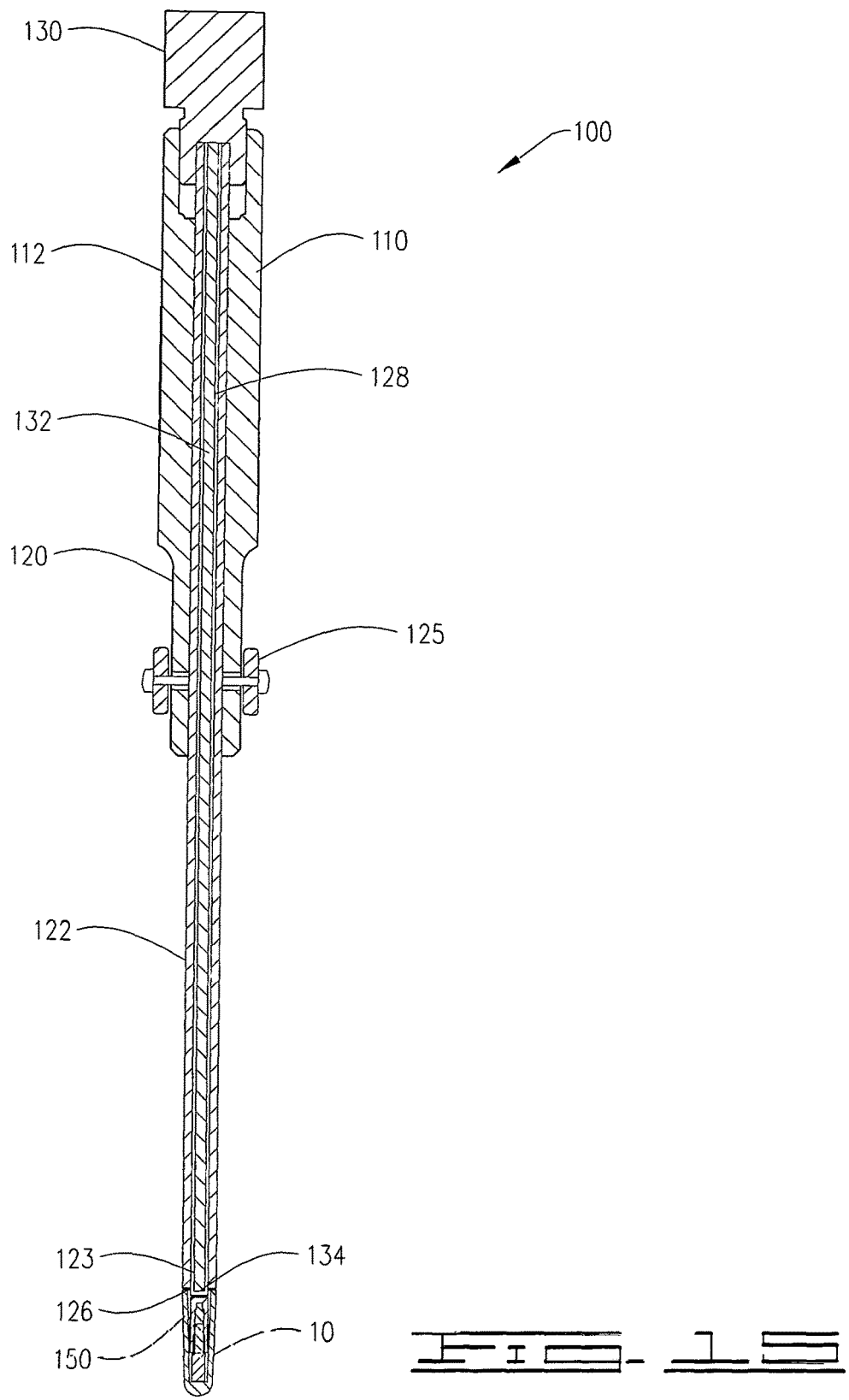
FIG. 15 is cross-sectional side view of the delivery tool and a suture anchor with a frangible nose ring.

The cooperating delivery tool 100, shown in FIGS. 14 and 15, comprises a hollow handle member 110 defining an outer grip portion 112, a hollow upper shaft 120 extending from the handle member 110, a suture tightening means 125, shown as at least one rotating knob connecting a rotating extension affixed to the upper shaft 120, a hollow lower shaft 122, with shaft bore 128 defined through the handle member 110, upper shaft 120 and lower shaft 122 leading through a connecting member 126 at a lower end 123 of the lower shaft 122. Within the shaft bore 128 is a retractable plunger 132 extending a plunger handle actuator 130 above the handle member 110 and a plunger tip 134 within the connecting member 126. The plunger 132 is moved downward or upward by pushing or pulling motions or by clockwise or counterclockwise motions on the plunger handle actuator 130, thereby extending or retracting the plunger tip 134 beyond and within the connecting member 126.

Figure 18:
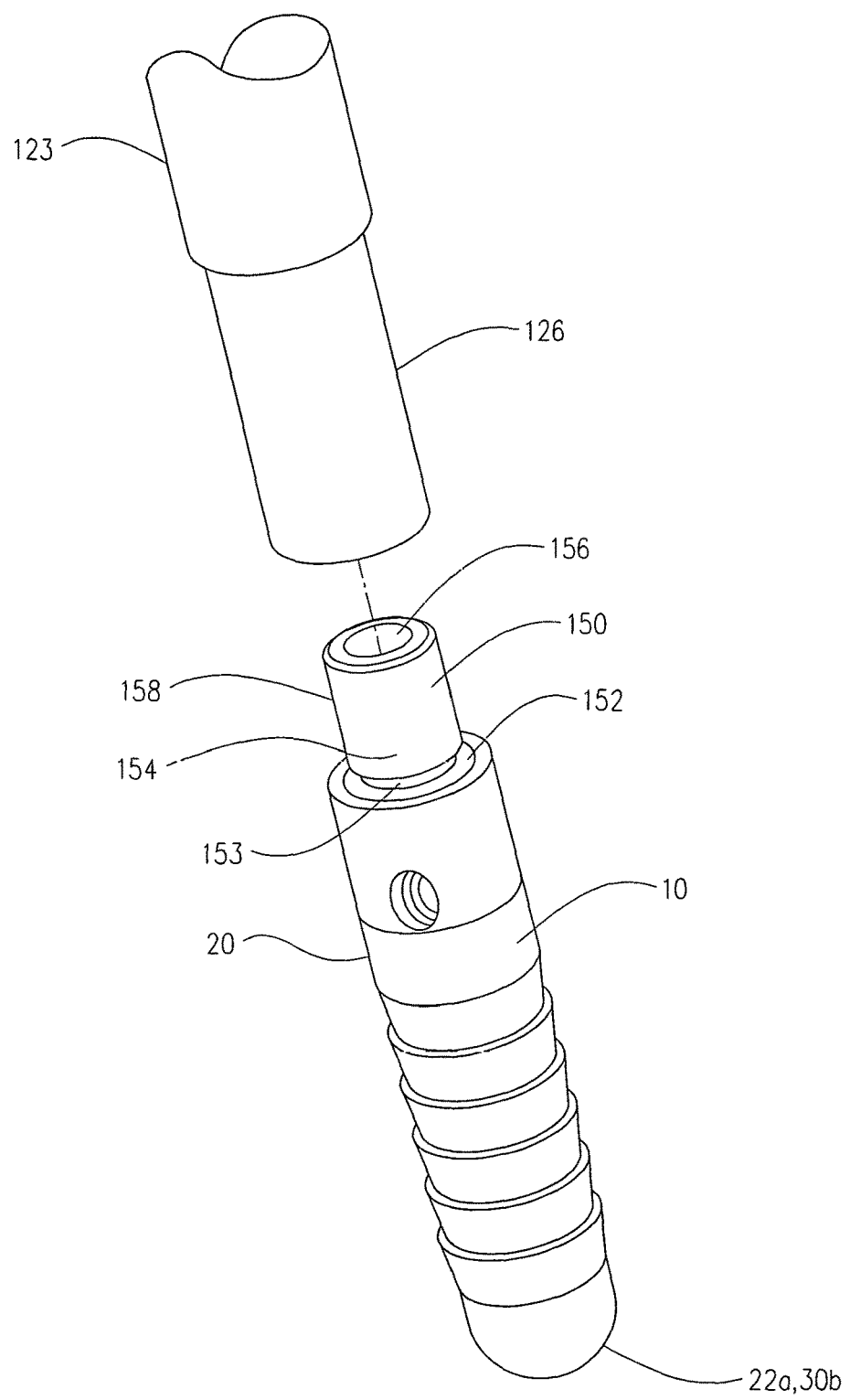
FIG. 18 is an isolated view of the tip of the delivery tool, a frangible nose ring and the first embodiment of the suture anchor.

The frangible ring connector 150 defines a lower frangible ring 152, FIGS. 16 and 17, identical in size, shape and purpose of the rotatable ring 60 used in the first and fourth embodiment, a frangible joint 153 connecting the lower frangible ring 152 to a body 154 which can be partially or completely fractured by intentional motion of the plunger handle actuator 130 when the delivery tool 100 is employed to install the suture anchor device 10, or by a shift of the delivery tool 100 from side to side once the lower frangible ring 152 is placed within the anchor body 20, FIG. 18. The body 154 of the frangible ring connector 150 may also define a frangible column 155, FIG. 17, instead of a frangible joint 153, FIG. 18. The eyelet pin 50 is disposed in the open position with the transverse passage co-linear to the connector suture passage 156. Sutures 200 that have already been placed in the soft tissue are manually placed with or without the use of a suture shuttle, through one end of the connector suture passage 156, into a corresponding end of the transverse passage 57 and retrieved from the other side of the connector suture passage 156. The suture is then passed outside of the lower shaft 122 and tensioned, further attached to the suture tightening means 25. An upper connector extension 158 further extends from the body 154 of the frangible ring connector 150 which inserts within the connecting member 126 of the delivery tool 100, FIGS. 14, 15 and 18.

Figure 22:
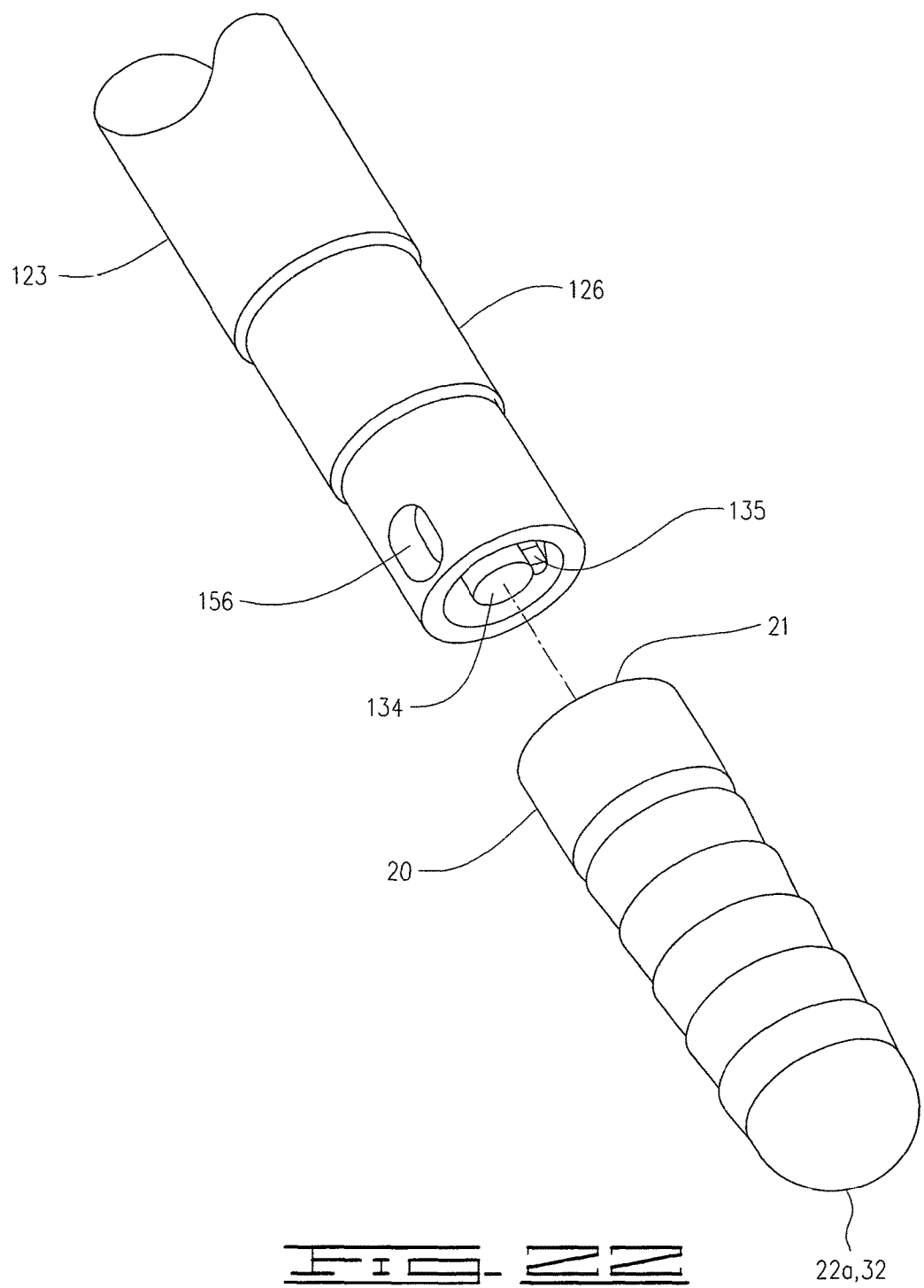
FIG. 22 is a lower perspective view of the connection components between key tool on the end of the tool plunger of the delivery tool and the suture anchor, suited for engagement with the tool portion of the eyelet pin and ring slot of FIG. 21.

After the frangible joint has been broken, the upper connector extension 158 remains connected to the end of the delivery tool 100, as shown in FIG. 22. Optionally, the plunger tip 134 may further comprise a ring notch key 135, FIG. 22, integrating and attaching to a key notch 65 in the rotatable ring 60, FIG. 21, to provide a secure and unique connection between the rotatable ring 60 or lower frangible ring 152 and the plunger tip 134 to rotate and otherwise manipulate the rotatable ring 60 or lower frangible ring 152 subsequent to fracture of the frangible joint 153 or frangible column 155. This would most generally occur after full deployment of the suture anchor device 10 and removal of the delivery tool 100 has taken place in the first or fourth embodiment.

Figure 29:
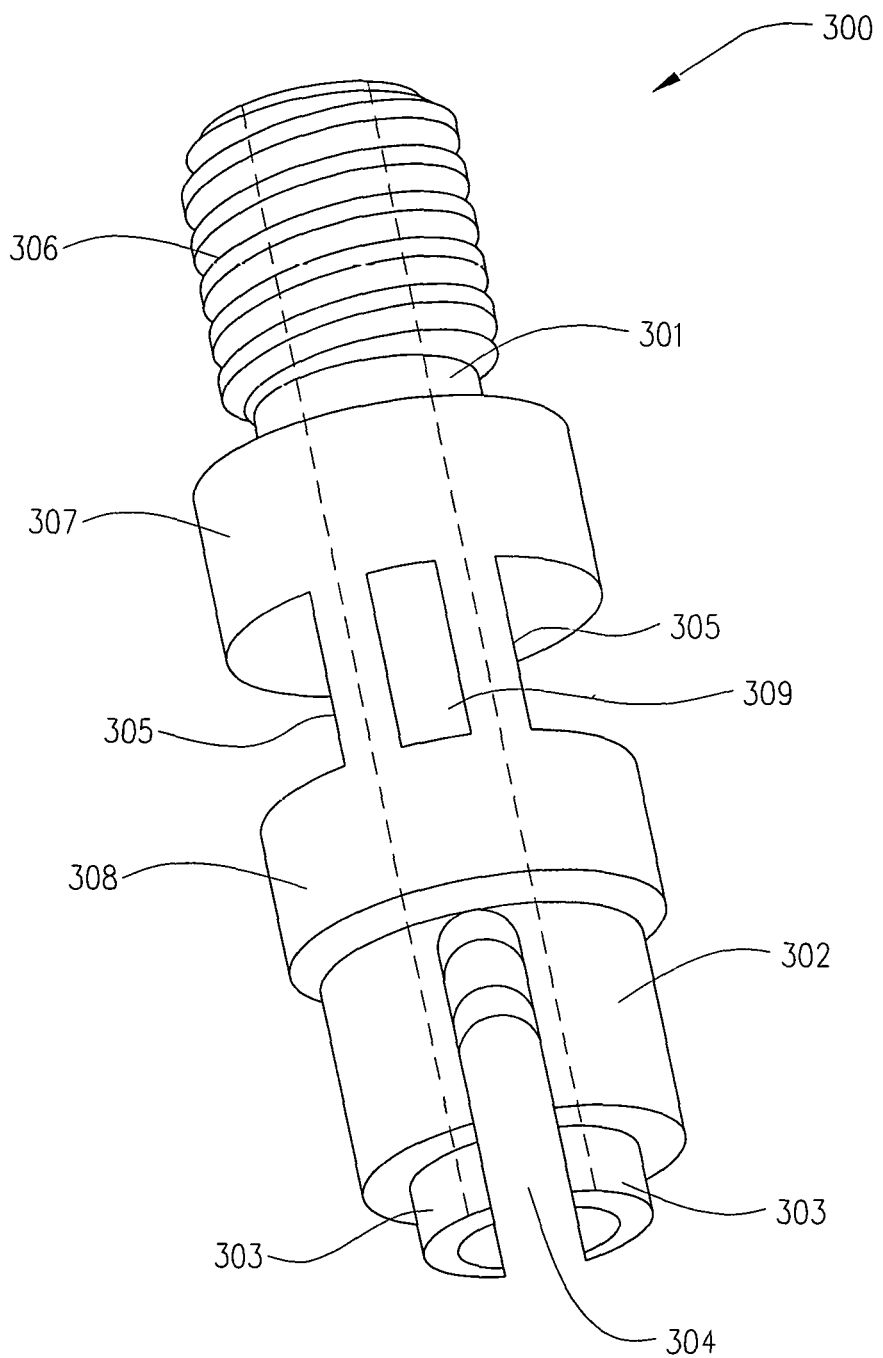
FIG. 29 is a perspective view of a multiple purpose disposable head optionally attaching to a handle or attaching to a delivery tool used to manipulate the various embodiments of the suture anchor devices.

The top locking rotatable suture anchor devices 10 described herein can incorporate a detachable head 300, provided that the lower end 122 of the delivery tool 100 of the shaft bore provides an internal thread, not shown. The delivery tool and the detachable head can be reusable or disposable. The detachable head, FIG. 29, defines a tool connecting end 301 extending a threaded head connector 306, an upper body 307 and a lower body 308, between which is extended a pair of jaw receptacles 305 and at least one transverse rectangular recess 309, the lower body extending a lower end 302 defining a pair of reduced diameter semi-circular flexible arches, the detachable head further defining a longitudinal suture channel 304. The flexible arches are provided to engage the space within the upper chamber expansion between the rotatable ring 60 and the proximal end 51 of the eyelet pin 50. This detachable head may be used as an adjustment tool to fine tune the rotary alignment or further depress deeper into bone any of the suture anchor devices 10 disclosed herein. The detachable head 300 may also be used in the embodiments of the suture anchor devices 10 not including the rotatable ring 60, which would be the second and third embodiments, the flexible arches 303 engaging the space between the upper end 21 of the anchor body and the eyelet expansion 59 of the eyelet pin, the detachable head 300 attaching to the delivery tool 100, or to another handle independently designed for the detachable head. The upper end of the eyelet pin, anchor body and rotatable ring can include slots, grooves or recesses for receiving the detachable head 300. The detachable head 300 may also be substituted upon the delivery tool 100 after fracture of the frangible joint 153 or frangible column 155 has been broken to prevent rough surfaces of the fractured components that might damage the sutures. The detachable head 300 may also be supplied as an integrated part of an independent tool use for insertion of the suture anchor device 10 into the bone, including a tap or awl.

Further, the rotatable suture anchor device 10 of the embodiments disclosed above may include several alternate features with the following more specific details. By example, the anchor body 20 may provide a cylindrical shape with the lower end 22a forming a bullet shape. The anchor body 20 may be made of the same or a different material than the central pin 40, the nose piece 30b, the eyelet pin 50 and the rotatable ring 60. By example, these components may be made of plastic and metal. The bone securing projections 24 may have a frustoconical shape, a wedge shape, or the shape of a barb, which may be circumferentially partial or full. The upper chamber expansion 26 might provide a square proximal edge having a greater diameter than the portion of the portions of the inner longitudinal chamber 25 and would conform is shape to the contour and shape of the rotatable ring 60 while securing the ring lock extension 29 within the ring lock groove 69, allowing the rotatable ring 60 to rotate, but not allowing elevation or removal of the rotatable ring 60 without intention. The tapered lower margin 66 of the rotatable ring 60 is provided to assist placement of the rotatable ring 60 within the upper chamber expansion 26 and past the ring lock extension 29 until engagement of the ring lock groove 69 with the ring lock extension 29 occurs.

In order to properly secure the central pin 40 in a static position once inserted into the inner longitudinal chamber 25, the expanded lower end 44 may be presented with an interference fit within the lower end 22a of the inner longitudinal chamber 25, be inserted within an upper pin orifice 36, be integrated with the nosepiece 30b or otherwise be held upright through other means. The slidable engagement between the cylindrical slide shaft 43 of the central pin 40 and the inner bore 53 of the eyelet pin 50 may provide respective smooth surfaces, textured surfaces, or means for incremental stage fitting, allowing the central pin 40 and eyelet pin 50 to be selectively positioned between the open position and the closed position. Additionally, the pin lock extensions 56 of the eyelet pin 50 may be provided in a plurality at multiple levels on the outer surface 55 engaging several circumferential inner locking grooves 28 along the cylindrical slide shaft 43 of the central pin, allowing for the same selective engagement and positioning between the pin lock extensions 56 and circumferential inner locking grooves 28 between the open and closed positions. Alternatively, the pin lock extensions 56 may be disposed on the cylindrical slide shaft 43 of the central pin 40 with locking grooves within the inner bore 53 of the eyelet pin 50. During engagement of the circumferential inner locking grooves 28 with the pin lock extensions 56 as well as the engagement of the ring lock groove 69 and ring lock extension 29, rotation of the eyelet pin 50 and rotating ring 60 is provided, thereby providing the full rotation of the suture 20 within the suture anchor device 10 in the closed position and the open position to fulfill the intention of the suture anchor device 10 over the prior art having a longitudinal axis rotation of the suture anchor device 10 to achieve proper angle of tension between an attached soft tissue and the rotatable suture anchor device 10 installed within a bone.

In accordance with the drawing figures, when the at least one suture 200 is located within the transverse passage 57, lowering the eyelet pin 50 into the closed position compresses the suture 200 between the roof 58 of the transverse passage 57 and upper end 46 of the central pin 40, FIGS. 1, 6, and 19, in the first embodiment between the proximal end 51 of the eyelet pin 50 and the inner opening 62 of the rotatable ring 60, and in the second embodiment between the upper chamber expansion 26 and the proximal end 51 of the eyelet pin 50, FIGS. 6 and 20. These locations of compression should be spaced apart at a distance which is appropriate to compress the at least one suture 200 to prevent movement of the suture 200 but not so close as to damage or deform the suture 200 to an extent that the suture integrity would be negatively affected.

The anchor body 20, rotatable ring 60, eyelet pin 50, and central pin 40 can be formed of any suitable biocompatible material of the first embodiment. One or more of the anchor body 20, rotatable ring 60, eyelet pin 50, and central pin 40 can include or be made of one or more of a metal, a metal alloy, magnesium alloy, or other absorbable metal alloy, or a polymer plastic. Materials that may be used in the suture anchor device 10 include, but are not limited to, titanium, stainless steel or cobalt-chrome alloys, polyethylene, poly-ether-ether-ketone (PEEK), poly-ether-amyl-ketone (PEAK); polylactide, polyglycolide, polyparadioxanone, polytrimethylene carbonate or polycaprolactone; or composites of the aforementioned with biocompatible inorganic substances such as carbon, hydroxyapatite, beta tricalcium phosphate, other calcium phosphate ceramics or calcium sulfate. In some embodiments, each of the anchor body 20, rotatable ring 60, eyelet pin 50, and central pin 40 can be made of the same material. In the second embodiment, the anchor body 20, the central pin 40, and the eyelet pin 50 can be made of plastic, such as PEEK, and the rotatable ring can be made of metal. In some embodiments, the anchor body 20 can be treated with or include a coating to improve stability and enhance fixation to bone. A trabecular tantalum coating can cover or partially cover an exterior surface of the anchor body 20. In some embodiments, such a coating can include pores allowing for bone growth into the coating, which can allow for additional fixation to the bone. In some embodiments, materials are selected for use in the suture anchor device 10 components that are one or more of biocompatible, corrosion resistant, resistant to biodegradation and bioresorption.

The rotatable suture device 10, described above with respect to FIGS. 1-22, can be used in procedures to treat a variety of medical conditions, but mostly concerning the reattachment of a soft tissue to a bone. Methods of delivering and/or using the suture anchor device 10 may include the following steps. First, the suture anchor device 10 can be secured to the delivery tool 100 through engagement of the lower frangible ring 152 or the rotatable ring 60 within the anchor body 20. In some embodiments, an initial suture 200, may be threaded through the transverse passage 57 of the eyelet pin 50 and connector suture passage 156 of the frangible ring connector 150, and then wrapped around the suture tightening means 125 in order to secure the suture 200 to the delivery tool 100. This suture 200 is not threaded through soft tissue, but rather can be used for securement. In some embodiments, the frangible ring connector 150 is preassembled to the suture anchor device 10 secured to the delivery tool 100.

Following securement of the suture anchor device 10 to the delivery tool 100, one or more sutures secured to soft tissue at a treatment site can be threaded through the transverse passage 57 and/or connector suture passages 156. In some embodiments, the sutures 200 are threaded using a suture threader, not shown. After the sutures 200 secured to soft tissue are threaded through the transverse passage 57 and/or the connector suture passages 156, the suture anchor 20 is advanced into bone at a treatment site via the delivery tool 100. After the suture anchor 20 is installed into bone, the sutures 200 can be tensioned and wrapped around the tightening means 125 of the delivery tool 100 in order to maintain the sutures 200 in a tensioned state. After the sutures 200 are wrapped around the tightening means 125, the eyelet pin 50 is advanced within the anchor body 20. The eyelet pin 50 can be advanced into the closed position by distally advancing the plunger 132 as described above. Advancement of the eyelet pin 50 within the anchor body 20 can secure the sutures 200 in place between the eyelet pin 50 and the central pin 40, between the eyelet pin 50 and the rotatable ring 60 and/or between the eyelet pin 50 and the suture anchor body 20. Downward advancement of the eyelet pin 50 can also lead to the fracture of the frangible joint 153 of the frangible ring connector 150, disengaging the lower frangible ring 152 within the anchor body 20. Following advancement of the eyelet pin 50 within the anchor body 20, the delivery tool 100 is be removed from the suture anchor device 10. Optionally, after the delivery tool 100 is removed, the sutures 200 can be tensioned using other known means or tools configured to advance the anchor body 20 further into bone without interfering with the sutures 200 secured within the suture anchor 20.

When the eyelet pin 50 is in the closed position with one or more sutures 200 located within the transverse passage 57, the eyelet pin 50 can be rotatable relative to the anchor body 20 around a longitudinal axis. In some embodiments, the central pin 40 can be configured to rotate relative to the anchor body 20 around the longitudinal axis. In some embodiments, the central pin 40 can be integrally formed with the nosepiece 30*b* and/or the anchor body 20. In some embodiments, the suture anchor 20 may not include a separate central pin 40. Rotation of the eyelet pin 50 within the anchor body 20 provides and encourages adjustment of the angle of the sutures 200 following installation. This can prevent additional stress on the sutures, and consequently, fraying or failure of the sutures due to installation at an improper angle. In some embodiments, the suture anchor device 10 is delivered to a surgeon with the eyelet pin 50 in the closed position.

In some embodiments, each frangible joint 153 may include separate frangible connections at one or more of the inner opening of the rotatable ring 60 and the outer surface 68 of the rotatable ring 60. In some embodiments, only one of the frangible columns 155 will include a frangible joint 153. In some embodiments, the frangible joint 153 and may be symmetric. In other embodiments, the frangible joint 153 may be asymmetric. The frangible joint 153 and may be fractured due to one or more of tensile and shear forces, as described above with respect to the frangible joint 153.

While the invention has been particularly shown and described with reference to a preferred embodiment thereof, it will be understood by those skilled in the art that changes in form and detail may be made therein without departing from the spirit and scope of the invention.

What is claimed is:

1. A top locking rotatable suture anchor device for orthopedic surgical procedures to attach soft tissue to a bone using one or more sutures providing adjustment of an angle of tension and rotation of an attached suture prior to, during and subsequent to installation in a bone, said rotatable suture anchor device comprising:

an anchor body defining an upper end, a lower end with a longitudinal axis there between, said body further defining an outer surface providing a plurality of bone securing projections, an inner longitudinal chamber along said longitudinal axis defining an inner wall providing at least one circumferential inner locking groove, and an upper chamber expansion;

a central pin disposed within said inner longitudinal chamber defining a base, an upward extending cylindrical slide shaft having an upper end with an annular space provided between said cylindrical slide shaft and said inner wall of said inner longitudinal chamber;

an eyelet pin defining a proximal end, a distal end, an inner bore having a lower bore opening, said inner bore slidably and rotatably engaging said cylindrical slide shaft within said annular space into an open position and a closed position, said eyelet pin further defining an outer surface extending at least one pin lock extension to lock said eyelet pin within said at least one circumferential inner locking groove into said closed position, and a transverse passage defined within an upper lock expansion at said proximal end receiving at least one suture through said transverse passage; and a rotatable ring defining an inner opening, an upper end, a lower end, an outer surface and a ring lock groove, said rotatable ring installed within said upper chamber expansion, said rotatable ring remaining fully rotatable about said longitudinal axis while longitudinally secured, said proximal end of said eyelet pin longitudinally moveable within said rotatable ring between said open and closed position, wherein said at least one suture is secured within said suture anchor device in said closed position within said transverse passage at a desired length and tension, with or without requiring a knot or tied connection to said suture anchor device, said at least one suture engaged between said proximal end of said eyelet pin and said inner surface of said rotatable ring, wherein said suture attachment may be knotless, knotted or tied to said suture anchor device, while still providing said suture fully rotatable around said longitudinal axis relative to the anchor body in said closed position.

2. The rotatable suture anchor device of claim 1, said central pin further defining an expanded lower end configured to secure within said inner longitudinal chamber.

3. The rotatable suture anchor device of claim 1, said central pin further defining said base is integrated with said lower end of said anchor body within said inner longitudinal chamber.

4. The rotatable suture anchor device of claim 1, wherein said anchor body is cylindrical and said bone securing projections define longitudinally spaced full or partial circumferential barbs, ridges or an axial thread.

5. The rotatable suture anchor device of claim 1, wherein said pin lock extensions and said inner locking grooves are disposed upon said inner bore of said eyelet pin and said cylindrical slide shaft of said cylindrical slide shaft.

6. The rotatable suture anchor device of claim 1, wherein said inner longitudinal chamber defines a plurality of circumferential inner locking grooves to engage a plurality of pin lock extensions on said outer surface of said eyelet pin and providing a plurality of selected positions between said open position and said closed position.

7. The rotatable sure anchor device of claim 1, said eyelet pin defusing the proximal end including an eyelet expansion, instead of or in addition to said ring lock expansion, said eyelet expansion further defining a recessed portion along said transverse passage providing said suture with passage from said eyelet pin within said rotatable ring without having to pass over said eyelet expansion or said ring lock expansion, allowing said suture to slide within said suture anchor device in a closed position.

8. The rotatable suture anchor device of claim 1, wherein said inner longitudinal chamber of said anchor body defines a lower chamber opening receiving and securing an upper plug end of a nose piece further providing an upper pin orifice to receive said base of said central pin.

9. The rotatable suture anchor device of claim 1, wherein said inner longitudinal chamber of said anchor body defines a lower chamber opening receiving and securing an upper plug end of a nose piece with said base of said central pin integrated with said upper plug end.

10. The rotatable suture anchor device of claim 1, said rotatable ring further defining a tapered lower margin below said ring lock groove to enhance advancement and securing of said rotatable ring within said upper chamber expansion as said ring lock extension of said anchor body engages said ring lock groove during installation.

11. The rotatable suture anchor device of claim 1, wherein said transverse passage and said inner bore of said eyelet pin intersect, allowing partial entry of said upper end of said central pin to intrude into said transverse passage when said suture anchor device is in a closed position, said upper end compressing said at least one suture against said roof of said transverse passage, providing further compression and security upon said at least one suture within said suture anchor device.

12. The rotatable suture anchor device of claim 1, further comprising a delivery tool defining a lower end providing a connecting member connecting a frangible ring connector extending a frangible lower ring, substituting for and identical to said rotatable ring, said frangible lower ring attaching to a body of said frangible ring connector by a frangible joint or at least one frangible column, wherein said frangible joint or column is broken subsequent to said frangible ring being inserted within said upper chamber expansion and engaged and retained by said ring lock extension of said anchor body, said delivery tool further providing a disposable head, interchangeable with said connecting member attaching to said lower end of said delivery tool by a tool connecting end, said disposable head further defining a lower end extending a pair of flexible arches which may engage said suture anchor device at said upper end of said anchor body between said rotatable ring and said eyelet expansion of said eyelet pin.

13. The rotatable suture anchor device of claim 1, further comprising:

a delivery tool defining a handle member with a grip portion, an upper shaft, a lower shaft, a suture tightening means between said upper shaft and lower shaft, a lower end defining a connecting member, a shaft bore extending through said handle member to said connecting member, said shaft bore receiving a plunger defining a plunger actuator extending above said grip portion, said plunger further defining a plunger tip situated within said connecting member, said plunger providing extension and retraction of said plunger within said shaft bore; and a frangible ring connector extending a frangible lower ring, substituting for and identical to said rotatable ring, said frangible lower ring attaching to a body of said frangible ring connector by a frangible joint or at least one frangible column, wherein said frangible joint or column is broken subsequent to said frangible ring being inserted within said upper chamber expansion and engaged and retained by said ring lock extension of said anchor body, wherein said plunger tip extending within said connecting member may be extended by advancement of said plunger handle actuator to advance said proximal end of said eyelet pin within said anchor body from said open position to said closed position to secure said at least one suture, wherein said delivery tool provides assistance on the installation of said rotatable suture anchor device within a bone, and wherein said delivery tool provides for the tensioning, adjustment, positioning and rotation of said suture secured within said rotatable suture anchor device.

14. The rotatable suture anchor device of claim 1, further comprising:
a delivery tool defining a handle;
a lower end with a connecting member; and
a plunger defining a plunger handle actuator above said handle,
wherein:
said plunger extends a plunger tip within said connecting member,
said plunger tip defines a ring notch key engaging a key notch of said rotatable suture anchor device,
said plunger tip is extendable from said connecting member by movement of said plunger handle actuator to apply pressure against said proximal end of said eyelet pin to move said proximal end of said eyelet pin from said open position to said closed position,
said delivery tool provides assistance on the installation of said rotatable suture anchor device within a bone,
said delivery tool provides for the tensioning of said suture through said suture tightening means engaging said suture through a connector suture passage within said connecting end,
said suture passing through said connector suture passage, through said shaft bore and engaging said suture tightening means, and
further adjustment, positioning and rotation of said suture secured within said rotatable suture anchor device is performed by said delivery tool.

15. A top locking rotatable suture anchor device for orthopedic surgical procedures to attach soft tissue to a bone using one or more sutures providing adjustment of an angle of tension and rotation of an attached suture prior to, during and subsequent to installation in a bone, said rotatable suture anchor device comprising:
an anchor body defining an upper end, a lower end with a longitudinal axis there between, said body further defining an outer surface providing a plurality of bone securing projections, an inner longitudinal chamber along said longitudinal axis defining an inner wall providing at least one circumferential inner locking groove, and an upper chamber expansion;

an eyelet pin defining a proximal end, a distal end, said eyelet pin further defining an outer surface extending at least one pin lock extension to lock said eyelet pin within said at least one circumferential inner locking groove into between an open and closed position, and a transverse passage defined within an upper lock expansion at said proximal end receiving at least one suture through said transverse passage; and a rotatable ring defining an inner opening, an upper end, a lower end, an outer surface and a ring lock groove, said rotatable ring installed within said upper chamber expansion, said rotatable ring remaining fully rotatable about said longitudinal axis while longitudinally secured, and said proximal end of said eyelet pin longitudinally moveable within said inner ring between said open and closed position,
wherein:
said at least one suture is secured within said suture anchor device in said closed position within said transverse passage at a desired length and tension, with or without requiring a knot or tied connection to said suture anchor device,
said at least one suture engaged between said proximal end of said eyelet pin and said inner surface of said rotatable ring, and
said suture attachment may be knotless, knotted or tied to said suture anchor device, while still providing said suture fully rotatable around said longitudinal axis relative to the anchor body in said closed position.

16. The rotatable suture anchor device of claim 15, said anchor body is cylindrical and said bone securing projections define longitudinally spaced full or partial circumferential barbs, ridges or an axial thread.

17. The rotatable suture anchor device of claim 15, wherein said inner cylindrical chamber defines a plurality of circumferential inner locking grooves to engage a plurality of pin lock extensions on said outer surface of said eyelet pin providing a plurality of selected positions between said open position and said closed position.

18. The rotatable sure anchor device of claim 15, said eyelet pin defining the proximal end including an eyelet expansion, instead of or in addition to said ring lock expansion, said eyelet expansion further defining a recessed portion along said transverse passage providing said suture with passage from said eyelet pin within said rotatable ring without having to pass over said eyelet expansion or said ring lock expansion, allowing said suture to slide within said suture anchor device in a closed position.

19. The rotatable suture anchor device of claim 15, wherein said inner longitudinal chamber of said anchor body defines a lower chamber opening receiving and securing an upper plug end of a nose piece.

20. The rotatable suture anchor device of claim 15, said rotatable ring further defining a tapered lower margin below said ring lock groove to enhance advancement and securing of said rotatable ring within said upper chamber expansion as said ring lock extension of said anchor body engages said ring lock groove during installation.

21. The rotatable suture anchor device of claim 15, further comprising a delivery tool defining a lower end providing a connecting member connecting a frangible ring connector extending a frangible lower ring, substituting for and identical to said rotatable ring, said frangible lower ring attaching to a body of said frangible ring connector by a frangible joint or at least one frangible column, wherein said frangible joint or column is broken subsequent to said frangible ring being inserted within said upper chamber expansion and engaged and retained by said ring lock extension of said anchor body.

22. The rotatable suture anchor device of claim 15, further comprising:
   a delivery tool defining:
      a handle member with a grip portion,
      an upper shaft,
      a lower shaft,
      a suture tightening means between said upper shaft and lower shaft,
      a lower end defining a connecting member, and
      a shaft bore extending through said handle member to said connecting member,
         said shaft bore receiving a plunger defining a plunger actuator extending above said grip portion,
         said plunger further defining a plunger tip situated within said connecting member, and
         said plunger providing extension and retraction of said plunger within said shaft bore;
   a frangible ring connector extending a frangible lower ring, substituting for and identical to said rotatable ring, said frangible lower ring attaching to a body of said frangible ring connector by a frangible joint or at least one frangible column,
   wherein:
      said frangible joint or column is broken subsequent to said frangible ring being inserted within said upper chamber expansion and engaged and retained by said ring lock extension of said anchor body,
      said plunger tip extends within said connecting member is extended by advancement of said plunger handle actuator to advance said proximal end of said eyelet pin within said anchor body from said open position to said closed position to secure said at least one suture,
      said delivery tool provides assistance on the installation of said rotatable suture anchor device within a bone, and
      said delivery tool provides tensioning, adjustment, positioning and rotation of said suture secured within said rotatable suture anchor device.

23. The rotatable suture anchor device of claim 15, further comprising:
   a delivery tool comprising:
      a handle,
      a lower end with a connecting member, and
      a plunger comprising a plunger handle actuator above said handle,
   wherein:
      said plunger extends a plunger tip within said connecting member,
      said plunger tip defines a ring notch key engaging a key notch of said rotatable suture anchor device,
      said plunger tip is extendable from said connecting member by movement of said plunger handle actuator to apply pressure against said proximal end of said eyelet pin to move said proximal end of said eyelet pin from said open position to said closed position,
      said delivery tool provides assistance on the installation of said rotatable suture anchor device within a bone,
      said delivery tool provides for the tensioning of said suture through said suture tightening means engaging said suture through a connector suture passage within said connecting end,
      said suture passing through said connector suture passage, through said shaft bore and engaging said suture tightening means,
      further adjustment, positioning and rotation of said suture secured within said rotatable suture anchor device is performed by said delivery tool,
      said delivery tool further provides a disposable head, interchangeable with said connecting member attaching to said lower end of said delivery tool by a tool connecting end, and
      said disposable head further comprises a lower end extending a pair of flexible arches that engage said suture anchor device at said upper end of said anchor body between said ring lock extension and said eyelet expansion of said eyelet pin.

* * * * *